US010479971B2

(12) United States Patent
Kagawa et al.

(10) Patent No.: US 10,479,971 B2
(45) Date of Patent: Nov. 19, 2019

(54) CELL CULTURE DEVICE AND CELL CULTURE METHOD

(71) Applicant: FUJIFILM CORPORATION, Minato-ku, Tokyo (JP)

(72) Inventors: Hideaki Kagawa, Kanagawa (JP); Shun Goto, Kanagawa (JP); Souichi Kohashi, Kanagawa (JP); Hidekazu Yamazaki, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 15/649,652

(22) Filed: Jul. 14, 2017

(65) Prior Publication Data
US 2017/0306279 A1  Oct. 26, 2017

Related U.S. Application Data

(63) Continuation of application No. PCT/JP2016/051602, filed on Jan. 20, 2016.

(30) Foreign Application Priority Data

Jan. 20, 2015  (JP) .................................. 2015-008718

(51) Int. Cl.
*C12M 3/00* (2006.01)
*C12M 1/00* (2006.01)
(Continued)

(52) U.S. Cl.
CPC ............ *C12M 21/08* (2013.01); *C12M 27/02* (2013.01); *C12M 29/00* (2013.01); *C12M 33/14* (2013.01); *C12M 47/20* (2013.01); *C12M 33/12* (2013.01)

(58) Field of Classification Search
CPC ....... C12M 29/04; C12M 29/14; C12M 29/18
See application file for complete search history.

(56) References Cited

U.S. PATENT DOCUMENTS 5,079,161 A * 1/1992 Mitsuda ................. C12M 25/16
435/174
5,166,067 A  11/1992 Ishida et al.
(Continued)

FOREIGN PATENT DOCUMENTS

CN  1814745 A  8/2006
CN  101796181 A  8/2010
(Continued)

OTHER PUBLICATIONS

Catharina Ellerstrom et al: ""Facilitated expansion of human embryonic stem cells by single-cell enzymatic dissociation", Stem Cells, Alphamed Press, Dayton, OH, US, vol. 25, No. 7, Jul. 1, 2007(Jul. 1, 2007), pp. 1690-1696, XP002678839, ISSN* 1066-5099. DOI:10. 1634/STEMCELLS. 2006-0607Retrived from the Internet:URL: http://onlinelibrary.wiley.com/doi/10.[retrieved on Mar. 22, 2007]* abstract*".

(Continued)

*Primary Examiner* — William H. Beisner
(74) *Attorney, Agent, or Firm* — Solaris Intellectual Property Group, PLLC

(57) ABSTRACT

A culture container has a first inflow port and a first outflow port. The first flow path connects the first outflow port to the first inflow port. A storage container is provided within the first flow path and has a second inflow port which is connected to the first outflow port and a second outflow port which is connected to the first inflow port. A second flow path connects a first region within the first flow path, and a second region within the first flow path. A division processing portion is provided within the second flow path, performs a division process of dividing a cell aggregation flowing in from the first flow path, and allows the cells subjected to the division process to flow out into the first flow path via the second region. A medium supply portion supplies a medium to the inside of the first flow path.

16 Claims, 23 Drawing Sheets

(51) Int. Cl.
C12M 1/06 (2006.01)
C12M 1/26 (2006.01)

(56) References Cited

U.S. PATENT DOCUMENTS

2004/0248077 A1* 12/2004 Rodriguez Rilo ..... C12M 29/18
435/4
2007/0238169 A1* 10/2007 Abilez .................. C12M 25/14
435/325
2010/0136690 A1 6/2010 Sundstrom et al.

FOREIGN PATENT DOCUMENTS

JP H02-150272 A 6/1990
JP H04-99483 A 3/1992

OTHER PUBLICATIONS

Extended European Search Report dated Mar. 6, 2018, issued in corresponding EP Patent Application No. 16740222.1.
English language translation of the following: Office action dated Apr. 2, 2019 from the SIPO in a Chinese patent application No. 201680006205.8 corresponding to the instant patent application.

* cited by examiner

DIVISION PROCESS

CELL CULTURE DEVICE AND CELL CULTURE METHOD

CROSS-REFERENCE TO RELATED APPLICATIONS

This application is a continuation application of International Application No. PCT/JP2016/051602, filed Jan. 20, 2016, the disclosure of which is incorporated herein by reference in its entirety. Further, this application claims priority from Japanese Patent Application No. 2015-008718, filed Jan. 20, 2015, the disclosure of which is incorporated herein by reference in its entirety.

BACKGROUND

1. Technical Field

The present invention relates to a cell culture device and a cell culture method.

2. Related Art

The present invention relates to a cell culture device and a cell culture system. For example, the following technologies are known. For example, a culture system of biological cells in which a film filtration separation device, a culture device, a medium storage tank, and a filtrate storage tank are connected to each other using liquid transfer pipes, into which a liquid transfer pump and a valve are inserted, has been disclosed in JP1990-150272A (JP-H2-150272A).

A culture device which enables continuous exchange of a medium by partially extracting a culture solution in which cells float, separating the culture solution and the cells from each other through a filtration film, and returning the cells to a culture tank together with a fresh medium has been disclosed in JP1992-99483A (JP-H4-99483A).

SUMMARY

It is considered that it is necessary to transplant $1 \times 10^9$ or more differentiated cells into a patient in order to treat, for example, hepatic disease or cardiac disease through cell transplantation. Therefore, development of mass culture technology of pluripotent stem cells is indispensable in order to realize the transplantation.

During the culture, for example, of pluripotent stem cells, problems may arise such that cells start to differentiate due to an adhesive fusion of cell aggregations (spheres), which have been generated through the culture of cells, if the sizes of the cell aggregations become too large, or such that cells in a central portion of a cell aggregation necrose. Accordingly, a division process in which a cell aggregation is divided at an appropriate timing during a period of culturing cells is necessary in order to prevent the size of the cell aggregation from becoming too large.

There is no example of a cell culture device which has been proposed so far and enables the production of a large amount of cells by continuously performing a series of processes, including the above-described division process, which are required for cell culture in a closed system. Therefore, it is difficult to increase the scale of culturing cells such as animal cells or stem cells, which have a relatively low proliferation rate. A countermeasure of installing cell culture devices in which human intervenes and of which the scale of culture is small in parallel can also be taken into consideration in order to deal with the increased scale of culture. However, in this case, the cost of the devices increases and the process becomes complicated. Furthermore, homogeneity of cells to be cultured, between the devices is deteriorated due to a difference in the culture environment which has been generated between the devices.

The present invention has been made in consideration of the above-described points and an object of the present invention is to provide a cell culture device which is capable of continuously performing a series of processes, which contains a division process and is required for cell culture, in a closed system, and a cell culture method in which such a cell culture device is used.

The cell culture device according to the present invention comprises: a culture container which has a first inflow port and a first outflow port and is used for culturing cells; a first flow path which connects the first outflow port to the first inflow port; a first storage container which is a storage container, which is provided within the first flow path and used for storing cells cultured in the culture container, the first storage container having a second inflow port which is connected to the first outflow port and a second outflow port which is connected to the first inflow port; a second flow path connecting a first region within the first flow path which is positioned between the second outflow port and the first inflow port, and a second region within the first flow path which is positioned between the second inflow port and the first outflow port; a division processing portion which is provided within the second flow path, performs a division process of dividing a cell aggregation, which is an aggregation of cells cultured in the culture container and flows in from the first flow path via the first region, and allows the cells subjected to the division process to flow out into the first flow path via the second region; and a medium supply portion which supplies a medium to the inside of the first flow path.

The cell culture device according to the present invention may further comprise: a first stirring portion which is provided between the second outflow port and the first inflow port within the first flow path and stirs a fluid flowing in. In the cell culture device according to the present invention, the first stirring portion may include a static mixer.

The cell culture device according to the present invention may further comprise: a first filter portion which is provided within a third flow path connecting the second inflow port to the second outflow port and performs a concentration process in which a liquid is removed from a mixture containing cells and the liquid accompanying the cells flowing out from the second outflow port. The first filter portion may include a tangential flow filter in the cell culture device according to the present invention.

The cell culture device according to the present invention may further comprise: a second storage container including a third outflow port and a third inflow port which is connected to the second inflow port; and a second filter portion which is provided within a fourth flow path connecting the third inflow port to the third outflow port and performs a concentration process in which a liquid is removed from a mixture containing cells and the liquid accompanying the cells flowing out from the third outflow port. In the cell culture device according to the present invention, the second filter portion may include a tangential flow filter. The cell culture device according to the present invention may alternately perform the concentration process using the first filter portion and the concentration process using the second filter portion.

The cell culture device according to the present invention may further comprise: a first pressure adjustment mechanism which adjusts a pressure within the first storage container; and a second pressure adjustment mechanism which adjusts a pressure within the second storage container.

In the cell culture device according to the present invention, the division processing portion may have a processing container for performing the division process and a third pressure adjustment mechanism which adjusts a pressure within the processing container.

The cell culture device according to the present invention may further comprise: a second stirring portion which is provided within a fifth flow path connecting the medium supply portion and the first flow path and stirs a fluid flowing in.

The cell culture device according to the present invention may further comprise: a cell supply portion which supplies cells cultured in the culture container to the first flow path.

The cell culture device according to the present invention may further comprise: a cell supply portion which is connected to a downstream side of the second stirring portion in the fifth flow path and supplies cells cultured in the culture container to the first flow path via the fifth flow path; and a third stirring portion which is provided on a downstream side of a region, to which the cell supply portion is connected, in the fifth flow path and stirs a fluid flowing in.

The cell culture device according to the present invention may further comprise: a freezing portion which is connected to a third region positioned between the second outflow port and the first outflow port, within the first flow path and freezes cells.

The cell culture device according to the present invention may further comprise: a pressure adjustment mechanism which adjusts a pressure within the culture container.

A cell culture method according to the present invention in which the above-described cell culture device is used, comprises: a medium exchange process of exchanging a used medium which has been used for culture of cells within the culture container with a new medium; and a division process of dividing a cell aggregation formed through culturing cells in the culture container. The medium exchange process includes a step of storing the cells cultured in the culture container in the first storage container together with a used medium, a step of removing the used medium from a mixture containing the cells and the used medium which have been stored in the first storage container, a step of supplying a new medium to the cells stored in the first storage container from the medium supply portion, and a step of accommodating the mixture containing the cells and the new medium in the culture container. The division process includes a step of dividing the cell aggregation formed within the culture container in the division processing portion, a step of exchanging a used medium which has been used for the culture of cells within the culture container with a new medium before or after dividing the cell aggregation in the division processing portion, and a step of accommodating the mixture containing the divided cells and the new medium in the culture container.

According to the present invention, there is provided a cell culture device which is capable of continuously performing a series of processes, which contains a division process and is required for cell culture, in a closed system, and a cell culture method in which such a cell culture device is used.

BRIEF DESCRIPTION OF THE DRAWINGS

Exemplary embodiments according to the technique of the present disclosure will be described in detail based on the following figures, wherein.

DETAILED DESCRIPTION

Figure 1:
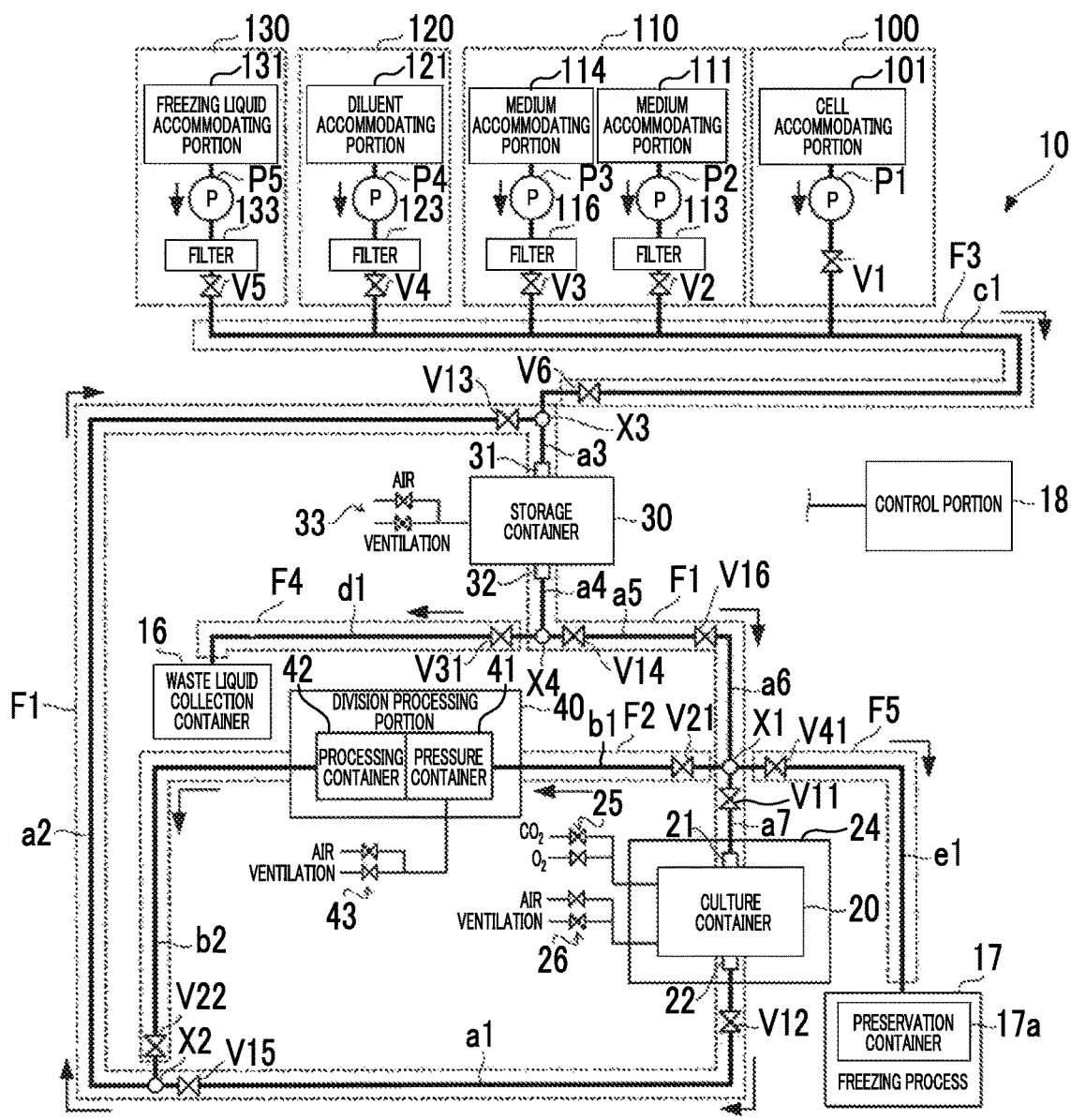
FIG. 1 is a view showing a configuration of a cell culture device according to a first embodiment of the present invention.

Hereinafter, an example of an embodiment of the present invention will be described while referring to drawings. The same reference numerals will be given to the same or equivalent components and portions in each drawing.

[First Embodiment]

FIG. 1 is a view showing a configuration of a cell culture device 10 according to a first embodiment of the present invention. The cell culture device 10 includes a cell supply portion 100, a medium supply portion 110, a diluent supply portion 120, and a freezing liquid supply portion 130. In addition, the cell culture device 10 includes a culture container 20, a storage container 30, a division processing portion 40, a waste liquid collection container 16, and a freezing portion 17.

The cell culture device 10 accommodates cells supplied from the cell supply portion 100 within the culture container 20 together with a medium (culture solution) supplied from the medium supply portion 110 and cultures the cells in a state in which the cells are made to, for example, float in the medium within the culture container 20.

<Cell Supply Portion>

The cell supply portion 100 has a cell accommodating portion 101 which accommodates cells to be cultured using the cell culture device 10 in a state where the cells are frozen; and a pump P1 which sends the cells accommodated in the cell accommodating portion 101 out into a flow path F3 including a pipe c1. In addition, the cell supply portion 100 has an on-off valve V1, which is provided on a downstream side of the pump P1, of a pipe connecting the cell accommodating portion 101 to the pipe c1. The cells accommodated in the cell accommodating portion 101 are sent out into the flow path F3 using the pump P1 being driven and the on-off valve V1 entering an open state.

Cells to be cultured using the cell culture device 10 according to the present embodiment are not particularly limited, all cells such as animal cells, plant cells, fungal cells, bacterial cells, protoplasts, established cell lines, and genetically modified artificial cells can be cultured.

An example of cells to be cultured is stem cells. The stem cells are not particularly limited as long as the stem cells have self-replication potency and differentiation potency, and may be pluripotent stem cells or somatic stem cells.

The pluripotent stem cells are cells having a self-replication potency and multiple differentiation potency which enables the cells to be differentiated into all of an ectoderm, a mesoderm, and an endoderm. Examples of the pluripotent stem cells include Embryonic Stem cells (ES cells), induced Pluripotent Stem cells (iPS cells), Embryonic Germ cells (EG cells), Embryonal Carcinoma cells (EC cells), Multipotent Adult Progenitor cells (MAP cells), Adult Pluripotent Stem cells (APS cells), and Multi-lineage differentiating Stress Enduring cells (Muse cells).

Examples of the somatic stem cells include mesenchymal stem cells, hematopoietic stem cells, and neural stem cells.

Other examples of cells to be cultured include somatic cells constituting a living body and progenitor cells thereof. Specific examples thereof include lymphocytes, neutrophils, monocytes, megakaryocytes, macrophages, fibroblasts, basal cells, keratinocytes, epithelial progenitor cells, pericytes, endothelial cells, adipose progenitor cells, myoblasts, osteoblasts, chondrocytes, hepatic parenchymal cells, pancreatic β cells, and gliocytes.

Other examples of cells to be cultured include animal cells such as Chinese hamster ovary (CHO), COS, HeLa, HepG2, C127, 3T3, BHK, HEK293, and Bowes melanoma cells; insect cells such as *Drosophila* S2 and *Spodoptera* Sf9; fungal cells such as yeast and *Aspergillus*; bacterial cells such as *Escherichia coli* and *Bacillus subtilis*; and plant cells and callus. These cells may be cells into which a protein expression vector is introduced for the purpose of a mass expression of proteins.

In a case of starting the cell culture in a state where the cells and a medium are accommodated in advance within the culture container 20, it is possible to omit the cell supply portion 100 in the cell culture device 10.

<Medium Supply Portion>

The medium supply portion 110 has: medium accommodating portions 111 and 114 accommodating a medium (culture solution) used for culturing of the cells; pumps P2 and P3 which send out media respectively accommodated in the medium accommodating portions 111 and 114 to the flow path F3; and filters 113 and 116 which are used for sterilizing the media respectively sent out from the pumps P2 and P3. In addition, the medium supply portion 110 has: an on-off valve V2, which is provided on a downstream side of the filter 113, of a pipe connecting the medium accommodating portion 111 to the pipe c1; and an on-off valve V3, which is provided on a downstream side of the filter 116, of a pipe connecting the medium accommodating portion 114 to the pipe c1. In this manner, the medium supply portion 110 according to the present embodiment has a medium supply function of two lines consisting of a first line including the medium accommodating portion 111, the pump P2, the filter 113, and the on-off valve V2, and a second line including the medium accommodating portion 114, the pump P3, the filter 116, and the on-off valve V3, and therefore, two media different from each other can be supplied. The number of lines in the medium supply portion 110 can be appropriately increased and decreased in accordance with a cell culture protocol or the like. That is, the medium supply portion 110 may be formed so as to supply three or more types of media, or may be formed so as to supply one medium. The medium accommodated in the medium accommodating portion 111 is sent out into the flow path F3 using the pump P2 being driven and the on-off valve V2 entering an open state. The medium accommodated in the medium accommodating portion 114 is sent out to the flow path F3 using the pump P3 being driven and the on-off valve V3 entering an open state.

Media which can be applied to a cell culture using the cell culture device 10 according to the present embodiment are not particularly limited, and all media can be applied. Specific examples thereof include liquid media such as a base medium for mammalian cells (for example, Dulbecco's Modified Eagle's Medium (DMEM), Dulbecco's Modified Eagle Medium: Nutrient Mixture F-12 (DMEM/F-12), Eagle's minimal essential medium (EMEM), Basal Medium Eagle (BME), Roswell Park Memorial Institute 1640 Medium (RPMI1640 Medium), E8 base medium, Skeletal Muscle Cell Basal Medium (SkBM), MCDB104, and MCDB153, 199, L15), a commercially available culture solution for maintaining stem cells, a base medium for insect cells, a medium for yeast, and a medium for bacteria.

Polymer compounds without cytotoxicity may be added to the media which can be applied to cell culture using the cell culture device 10 according to the present embodiment for the purpose of continuously floating the cells and/or the purpose of preventing the cells from being closely attached to each other. Examples of the polymer compounds added to the media for the above-described purposes include a polymer compound that adjusts a specific gravity of a medium, a polymer compound that adjusts viscosity of a medium, and a polymer compound that forms a three-dimensional network structure in a medium. Examples of such polymer compounds include polysaccharides such as cellulose, methylcellulose, carboxymethyl cellulose, gellan gum, deacylated gellan gum, hyaluronic acid, alginic acid, carrageenan, xanthan gum, diutan gum, starch, and pectin; proteins such as collagen and gelatin; synthetic polymers such as polyethylene glycol and polyvinyl pyrrolidone.

Various types of generally addable components, for example, antibiotics such as penicillin and streptomycin; vitamins such as ascorbic acid and retinoic acid, or vitamin derivatives; sugar sources such as glucose; amino acids; mineral salts; serum or serum substitutes; proteins such as transferrin; hormones such as insulin; growth factors; differentiation inhibitory factors; antioxidants such as 2-mercaptoethanol and dithiothreitol; metal ions such as a calcium ion, a magnesium ion, a zinc ion, an iron ion, and a copper ion may be added to the media which can be applied to the cell culture using the cell culture device 10 according to the embodiment.

<Diluent Supply Portion>

The diluent supply portion 120 has: a diluent accommodating portion 121 which accommodates a diluent to be used for a diluting process to be appropriately performed during a cell culture process; a pump P4 which sends the diluent accommodated in the diluent accommodating portion 121 out into the flow path F3; and a filter 123 which is used for sterilizing the diluent sent out from the pump P4. In addition, the diluent supply portion 120 has: an on-off valve V4, which is provided on a downstream side of the filter 123, of a pipe connecting the diluent accommodating portion 121 to the pipe c1. The diluent accommodated in the diluent accommodating portion 121 is sent out into the flow path F3 using the pump P4 being driven and the on-off valve V4 entering an open state.

The diluent which can be applied to the cell culture using the cell culture device 10 according to the present embodiment is not particularly limited, and examples of the diluent include a base medium for mammalian cells (for example, DMEM, DMEM/F-12, MEM, DME, RPMI1640, MCDB104, 199, MCDB153, L15, SkBM, Basal Medium, or E8 base medium). In a case where the diluting process is unnecessary in the cell culture process, it is possible to omit the diluent supply portion 120.

<Freezing Liquid Supply Portion>

The freezing liquid supply portion 130 has: a freezing liquid accommodating portion 131 which accommodates a freezing liquid used in a case of cryopreservation of cultured cells in the freezing portion 17; a pump P5 which sends the freezing liquid accommodated in the freezing liquid accommodating portion 131 out into the flow path F3; and a filter 133 which is used for sterilizing the freezing liquid sent out from the pump P5. In addition, the freezing liquid supply portion 130 has an on-off valve V5, which is provided on a downstream side of the filter 133, of a pipe connecting the freezing liquid accommodating portion 131, the pump P5, and the filter 133. The freezing liquid accommodated in the freezing liquid accommodating portion 131 is sent out into the flow path F3 using the pump P5 being driven and the on-off valve V5 entering an open state. In a case where it is unnecessary to cryopreserve the cultured cells, it is possible to omit the freezing liquid supply portion 130 in the cell culture device 10.

<Culture Container>

The culture container 20 is a container for accommodating the cells supplied from the cell supply portion 100 together with a medium supplied from the medium supply portion 110 and culturing the accommodated cells. The form of the culture container 20 is not particularly limited, and it is possible to use a container made of glass or stainless steel, or a container having a form of a plastic bag. The culture container 20 has an inflow port 21 for allowing the cells and a medium to flow into the culture container 20 and an outflow port 22 for allowing the cells and the medium which have been accommodated in the culture container 20 to flow out to the outside of the culture container 20.

The culture container 20 can be accommodated in an incubator 24, which is airtight closed and of which the temperature is controlled to, for example, 30° C. to 40° C. (preferably 37° C.) and the $CO_2$ concentration is controlled to, for example, 2% to 10% (preferably 5%). The incubator 24 includes a gas supply mechanism 25 for supplying oxygen ($O_2$) and carbon dioxide ($CO_2$) to the cells accommodated in the culture container 20 together with a medium. In addition, the incubator 24 includes a pressure adjustment mechanism 26 which adjusts the pressure within the culture container 20. The pressure adjustment mechanism 26 pressurizes the atmosphere within the culture container 20 by introducing air into the culture container 20, or releases the atmosphere within the culture container 20 into the air by discharging the atmosphere within the culture container 20 to the outside. The pressure adjustment mechanism 26 allows the cells and a medium which have been accommodated in the culture container 20 to flow into a circulation flow path F1 by increasing the pressure within the culture container 20 more than the pressure within the circulation flow path F1 to be described below.

<Circulation Flow Path>

The cell culture device 10 has the circulation flow path F1 including pipes a1 to a7 connecting the outflow port 22 to the inflow port 21 of the culture container 20. Cells and a medium which have been accommodated in the culture container 20 circulate within the circulation flow path F1 in a culture process. The cells and the medium flowing inside the circulation flow path F1 flow into the culture container 20 via the inflow port 21, and the cells and the medium which have been accommodated inside the culture container 20 flow out to the inside the circulation flow path F1 via the outflow port 22.

An on-off valve V11 is provided in the pipe a7 forming the circulation flow path F1 connected to the inflow port 21 of the culture container 20. An on-off valve V12 is provided in the pipe a1 forming the circulation flow path F1 connected to the outflow port 22 of the culture container 20. The on-off valve V11 is made to enter an open state in a case where the cells and a medium are allowed to flow into the culture container 20 from the circulation flow path F1 and is made to enter a closed state in other cases. The on-off valve V12 is made to enter an open state in a case where the cells and a medium are allowed to flow out from the inside of the culture container 20 to the inside of the circulation flow path F1 and is made to enter a closed state in other cases.

The flow path F3 formed by the pipe c1 connected to the cell supply portion 100, the medium supply portion 110, the diluent supply portion 120, and the freezing liquid supply portion 130 is connected to the circulation flow path F1 in a connection region X3. That is, cells accommodated in the cell accommodating portion 101, media respectively accommodated in the medium accommodating portions 111 and 114, a diluent accommodated in the diluent accommodating portion 121, and a freezing liquid accommodated in the freezing liquid accommodating portion 131 are supplied to the circulation flow path F1 via the flow path F3 and the connection region X3.

An on-off valve V6 is provided in the vicinity of the connection region X3 in the pipe c1 forming the flow path F3. The on-off valve V6 is made to enter an open state in a case where the cell supply portion 100, the medium supply portion 110, the diluent supply portion 120, and the freezing liquid supply portion 130 respectively supplies cells, a medium, a diluent, and a freezing liquid to the inside of the circulation flow path F1 and is made to enter a closed state in other cases.

<Storage Container>

The storage container 30 is provided within the circulation flow path F1, that is, in the middle of the circulation flow path F1. The storage container 30 is a container for temporarily storing cells, a medium, a diluent, and a freezing liquid flowing inside the circulation flow path F1, and is used in a subculture process, a medium exchange process, a division process, and a freezing process to be described below which are performed during a culture period. The form of the storage container 30 is not particularly limited, and it is possible to use, for example, a container made of glass or stainless steel or a container having a form of a plastic bag.

The storage container 30 has: an inflow port 31 for allowing cells, a medium, a diluent, and a freezing liquid flowing inside the circulation flow path F1 to flow into the storage container 30; and an outflow port 32 for allowing the cells, the medium, the diluent, and the freezing liquid which have been accommodated in the storage container 30 to flow out to the inside the circulation flow path F1. The inflow port 31 of the storage container 30 is connected to the outflow port 22 of the culture container 20 using the pipes a1 to a3 forming the circulation flow path F1. The outflow port 32 of the storage container 30 is connected to the inflow port 21 of the culture container 20 using the pipes a4 to a7 forming the circulation flow path F1. In addition, in the present embodiment, the connection region X3 to which the circulation flow path F1 and the flow path F3 are connected is disposed in the vicinity of the inflow port 31 of the storage container 30. However, the connection position between the circulation flow path F1 and the flow path F3 can be disposed at any position within the circulation flow path F1.

An on-off valve V13 is provided in the vicinity of the inflow port 31 of the storage container 30 in the pipe a2 forming the circulation flow path F1. The on-off valve V13 is made to enter an open state in a case where cells, a medium, and the like are allowed to flow into the storage container 30 from the circulation flow path F1 and is made to enter a closed state in other cases. In addition, an on-off valve V14 is provided in the vicinity of the outflow port 32 of the storage container 30 in the pipe a5 forming the circulation flow path F1. The on-off valve V14 is made to enter an open state in a case where cells, a medium, and the like within the circulation flow path F1 are transferred to the culture container 20, the division processing portion 40, and the freezing portion 17 from the inside of the storage container 30, and is made to enter a closed state in other cases.

The storage container 30 includes a pressure adjustment mechanism 33 which adjusts the pressure within the storage container 30. The pressure adjustment mechanism 33 pressurizes the atmosphere within the storage container 30 by introducing air into the storage container 30, or releases the atmosphere within the storage container 30 into the air by discharging the atmosphere within the storage container 30 to the outside. The pressure adjustment mechanism 33 allows cells, a medium, a diluent, and a freezing liquid which have been stored in the storage container 30 to flow out into the circulation flow path F1 from the outflow port 32 by increasing the pressure within the storage container 30 more than the pressure within the circulation flow path F1.

The cell culture device 10 has a flow path F2 including pipes b1 and b2 which connect a connection region X1 positioned between the outflow port 32 of the storage container 30 and the inflow port 21 of the culture container 20, within the circulation flow path F1, to a connection region X2 positioned between the inflow port 31 of the storage container 30 and the outflow port 22 of the culture container 20, within the circulation flow path F1. Cells, a medium, and the like flowing inside the circulation flow path F1 can flow into the flow path F2 via the connection region X1. In addition, cells, a medium, and the like flowing inside the flow path F2 can flow into the circulation flow path F1 via the connection region X2.

<Division Processing Portion>

The division processing portion 40 is provided within the flow path F2, that is, in the middle of the flow path F2. The division processing portion 40 includes a processing container 42 for performing a division process in which a cell aggregation generated by culturing the cells within the culture container 20 is divided. The division process performed within the processing container 42 may be a mechanical division process or may be an enzymatic process in which a cell dissociation enzyme is used. In a case where a mechanical division process is applied, a mesh filter (not shown in the drawing) can be disposed inside the processing container 42. By making a cell aggregation pass through the mesh filter, the cell aggregation is divided into a size in accordance with the mesh size of the mesh filter. In contrast, in a case where a division process using an enzymatic process is applied, a cell dissociation enzyme such as trypsin-ethylenediaminetetraacetic acid (EDTA) can be accommodated in the processing container 42. The cell aggregation is divided by immersing the cell aggregation in the cell dissociation enzyme over a certain period of time.

The division processing portion 40 divides a cell aggregation flowing into the flow path F2 via the connection region X1 from the circulation flow path F1, in the processing container 42. The cells which have been subjected to the division process flow out into the circulation flow path F1 via the connection region X2.

The division processing portion 40 includes: a pressure container 41 communicating with the processing container 42; and a pressure adjustment mechanism 43 which adjusts the pressure within the pressure container 41 and the processing container 42. The pressure adjustment mechanism 43 pressurizes the atmosphere within the pressure container 41 and the processing container 42 by introducing air into the pressure container 41, or releases the atmosphere within the pressure container 41 and the processing container 42 into the air by discharging the atmosphere within the pressure container 41 to the outside. The pressure adjustment mechanism 43 allows cells which have been subjected to a division process to flow out into the circulation flow path F1 by increasing the pressure within the pressure container 41 and the processing container 42 more than the pressure within the circulation flow path F1.

An on-off valve V21 is provided in the vicinity of the connection region X1 in the pipe b1 which forms the flow path F2 and is disposed on an upstream side of the division processing portion 40. The on-off valve V21 is made to enter an open state in a case where cells or the like are transferred to the division processing portion 40 from the storage container 30, and is made to enter a closed state in other cases. In contrast, an on-off valve V22 is provided in the vicinity of the connection region X2 in the pipe b2 which forms the flow path F2 and is disposed on a downstream side of the division processing portion 40. The on-off valve V22 is made to enter an open state in a case where cells or the like which have been subjected to a division process using the division processing portion 40 are made to flow out into the circulation flow path F1, and is made to enter a closed state in other cases.

An on-off valve V15 is provided on an upstream side of the connection region X2 and in the vicinity of the connection region X2 in the pipe a1 forming the circulation flow path F1. The on-off valve V15 is made to enter an open state in a case where cells, a medium, and the like are transferred to the storage container 30 from the culture container 20, and is made to enter a closed state in other cases.

<Waste Liquid Collection Container>

The cell culture device 10 has a flow path F4 including a pipe dl connected to the circulation flow path F1 in a connection region X4 positioned between the outflow port 32 of the storage container 30 and the inflow port 21 of the culture container 20 within the circulation flow path F1 on an upstream side (closer to the storage container 30) further than the connection region X1. The waste liquid collection container 16 is provided at an end portion of the flow path F4. The waste liquid collection container 16 is a container for collecting a waste liquid flowing into the flow path F4 via the connection region X4 from the circulation flow path F1. A used medium, a used diluent, and a freezing liquid or the like accompanying the cells supplied from the cell supply portion 100 in a frozen state are included in the waste liquid collected in the waste liquid collection container 16. The form of the waste liquid collection container 16 is not particularly limited, and it is possible to use, for example, a container made of glass or stainless steel or a container having a form of a plastic bag.

An on-off valve V31 is provided in the vicinity of the connection region X4 in the pipe dl forming the flow path F4. The on-off valve V31 is made to enter an open state in a case where a waste liquid flowing out from the storage container 30 is collected within the waste liquid collection container 16, and is made to enter a closed state in other cases.

<Freezing Portion>

The cell culture device 10 has a flow path F5 including a pipe e1 connected to the circulation flow path F1 in the connection region X1. The freezing portion 17 is provided at an end portion of the flow path F5. The freezing portion 17 has a preservation container 17a accommodating the cells flowing into the flow path F5 via the connection region X1 from the circulation flow path F1 together with a freezing liquid supplied from the freezing liquid supply portion 130. The preservation container 17a may have a form of, for example, a vial, a cryo tube, or a bag. The freezing portion 17 can include a freezer freezing cells or a freezing liquid which have been accommodated in the preservation container 17a. In addition, the freezing portion 17 may include a tank filled with liquid nitrogen or may be constituted so as to accommodate the preservation container 17a in a tank. In addition, the freezing portion 17 may include, for example, a CRYO LIBRARY (registered trademark) system manufactured by TAIYO NIPPON SANSO CORPORATION. An on-off valve V41 is provided in the vicinity of the connection region X1 in the pipe e1 forming the flow path F5. The on-off valve V41 is made to enter an open state in a case where the cells and a freezing liquid are transferred into the freezing portion 17 from the storage container 30, and is made to enter a closed state in other cases. The connection position between the flow path F5 and the circulation flow path F1 may be any position as long as the position is between the outflow port 32 of the storage container 30 and the inflow port 21 of the culture container 20. In addition, in a case where it is unnecessary to cryopreserve the cells, it is possible to omit the freezing portion 17.

<Control Portion>

A control portion 18 integrally controls operations of the pumps P1 to P5, the on-off valves V1 to V5, V11 to V16, V21, V22, V31, and V41, the gas supply mechanism 25, and the pressure adjustment mechanisms 26, 33, and 43. Accordingly, culturing of cells in accordance with a predetermined cell culture protocol is automatically performed without human intervention. The electrical connection wiring between the control portion 18 and each of the above-described components controlled by the control portion 18 is not shown in FIG. 1 from the viewpoint of avoiding complications of the drawing.

The culture container 20 is an example of a culture container of the present invention. The inflow port 21 of the culture container 20 is an example of a first inflow port in the present invention. The outflow port 22 of the culture container 20 is an example of a first outflow port in the present invention. The storage container 30 is an example of a storage container in the present invention. The inflow port 31 of the storage container 30 is an example of a second inflow port in the present invention. The outflow port 32 of the storage container 30 is an example of a second outflow port in the present invention. The circulation flow path F1 is an example of a first flow path in the present invention. The flow path F2 is an example of a second flow path in the present invention. The connection region X1 is an example of a first region in the present invention. The connection region X2 is an example of a second region in the present invention. The division processing portion 40 is an example of a division processing portion in the present invention. The processing container 42 is an example of a processing container in the present invention. The pressure adjustment mechanism 43 is an example of a third pressure adjustment mechanism included in the division processing portion in the present invention. The cell supply portion 100 is an example of a cell supply portion in the present invention. The medium supply portion 110 is an example of a medium supply portion in the present invention. The flow path F3 is an example of a fifth flow path in the present invention. The freezing portion 17 is an example of a freezing portion in the present invention.

Hereinafter, an example of a process which can be performed in the cell culture device 10 according to the present embodiment will be shown. The cell culture device 10 performs, for example, a subculture process, a medium exchange process, a division process, and a freezing process exemplified below. The subculture process, the medium exchange process, the division process, and the freezing process described below are realized by the control portion 18 controlling the operation of the on-off valves V1 to V5, V11 to V16, V21, V22, V31, and V41, the pumps P1 to P5, and the pressure adjustment mechanisms 26, 33, and 43.

<Subculture Process>

Figure 2:
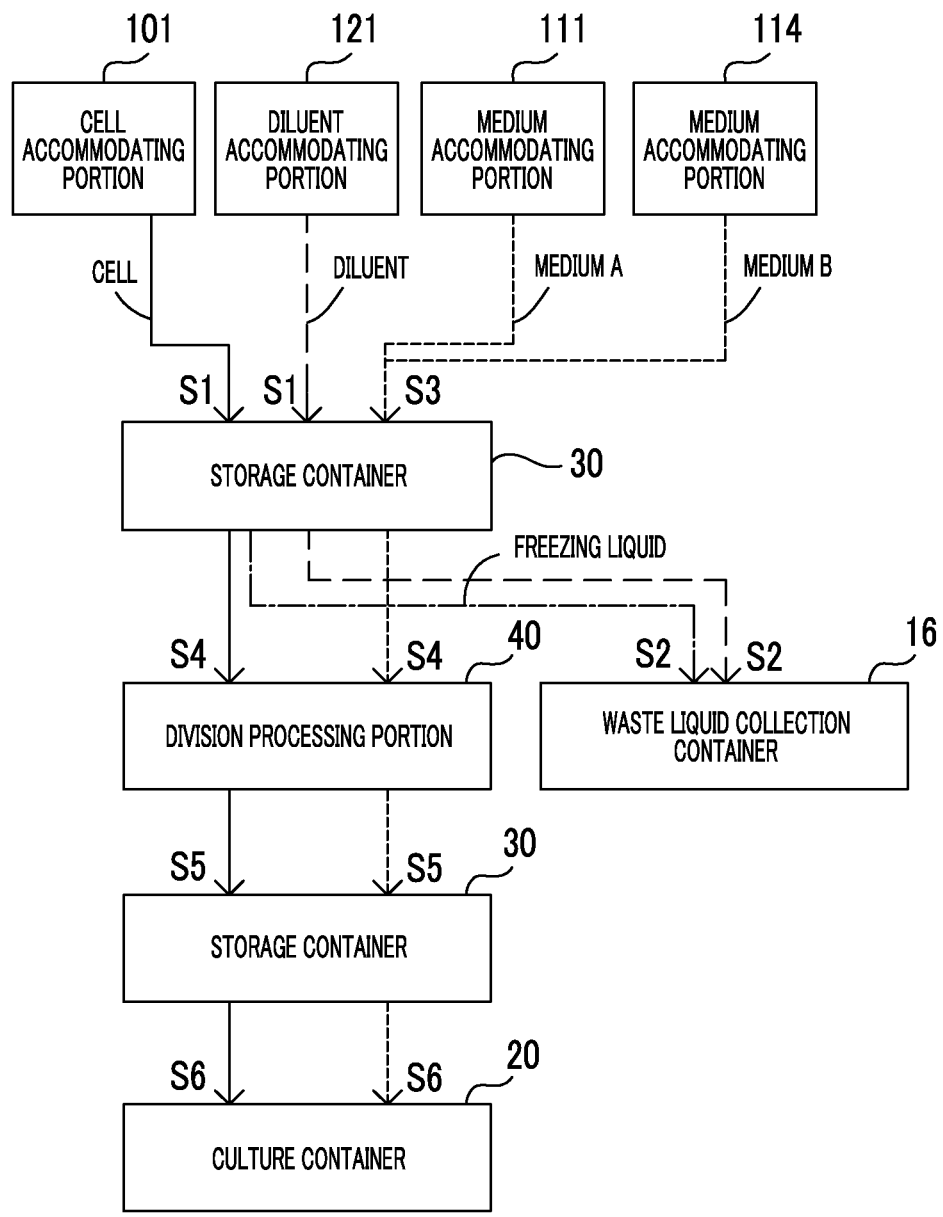
FIG. 2 is a view showing a flow of cells or the like in a case of performing a subculture process in the cell culture device according to the first embodiment of the present invention.

The cell culture device 10 performs a subculture process as follows in which cell culture is started by accommodating the cells accommodated in the cell accommodating portion 101 in the culture container 20 together with the media accommodated in the medium accommodating portions 111 and 114. In the following description, a case where a division process in the division processing portion 40 is a mechanical division process will be exemplified. FIG. 2 is a view showing a flow of cells, media, and the like in a case where the cell culture device 10 performs a subculture process in the cell culture device 10. A correspondence between the flow of cells, media, and the like and each processing step shown below is shown in FIG. 2.

In Step S1, the on-off valves V1, V4, and V6 are made to enter an open state and the pumps P1 and P4 are driven. Accordingly, the cells accommodated in the cell accommodating portion 101 in a frozen state and the diluent accommodated in the diluent accommodating portion 121 flow into the storage container 30 via the flow path F3 and the circulation flow path F1.

In Step S2, a concentration process in which a freezing liquid and a diluent are removed from a mixture which contains the cells, the freezing liquid, and the diluent and is stored in the storage container 30, the freezing liquid and the diluent accompanying the cells, is performed. The above-described concentration process is performed, for example, by precipitating (naturally precipitating) the cells, which have been accommodated in the storage container 30 together with the diluent, in the storage container 30 and removing a supernatant liquid containing the diluent and the freezing liquid. Specifically, the cells are precipitated in the storage container 30, and then, the on-off valve V14 is made to enter an open state for a short period of time. Accordingly, the cells are allowed to flow out from the storage container 30 while allowing the supernatant liquid to remain in the storage container 30, and are allowed to stay within the pipe a5. Thereafter, the on-off valve V14 is made to enter a closed state and the on-off valve V31 is made to enter an open state. Accordingly, a waste liquid containing the diluent and the freezing liquid remaining in the storage container 30 flows out from the outflow port 32 of the storage container 30 and is collected in the waste liquid collection container 16 via the flow path F4. Transferring of the cells to the pipe a5 from the storage container 30 and transferring of the diluent and the freezing liquid to the waste liquid collection container 16 from the storage container 30 are performed using the pressure adjustment mechanism 33 pressurizing the atmosphere within the storage container 30.

In Step S3, the on-off valves V2, V3, and V6 are made to enter an open state and the pumps P2 and P3 are driven. Accordingly, a medium A and a medium B which have been accommodated in the medium accommodating portions 111 and 114 flow into the storage container 30 via the flow path F3 and the circulation flow path F1. Thereafter, the on-off valve V14 is made to enter an open state, and a mixed medium consisting of the medium A and the medium B flows out from the storage container 30 and joins to the cells staying in the pipe a5.

In Step S4, the on-off valves V14, V16, and V21 are made to enter an open state. In addition, the atmosphere within the storage container 30 is pressurized by the pressure adjustment mechanism 33. Accordingly, the cells and the media which have been staying in the pipe a5 flow into the flow path F2 via the connection region X1 and flow into the division processing portion 40. The cells flowing into the division processing portion 40 are subjected to a division process within the processing container 42. The division process referred to herein is performed for the purpose of crushing the cells which have been in a frozen state.

In Step S5, the on-off valves V22 and V13 are made to enter an open state. In addition, the atmosphere within the pressure container 41 and the processing container 42 is pressurized by the pressure adjustment mechanism 43. Accordingly, the cells which have been subjected to the division process flow out into the circulation flow path F1 via the connection region X2 together with the media and are transferred into the storage container 30.

In Step S6, the on-off valves V14, V16, and V11 are made to enter an open state. In addition, the atmosphere within the storage container 30 is pressurized by the pressure adjustment mechanism 33. Accordingly, the cells and the media which have been stored in the storage container 30 flow into the culture container 20 via the circulation flow path F1. The subculture process is completed through the process of the above-described Steps S1 to S6.

In the above-described example, the concentration process and the supply of a new medium are performed before the division process. However, the concentration process and the supply of a new medium may be performed after the division process.

<Medium Exchange Process>

Figure 3:
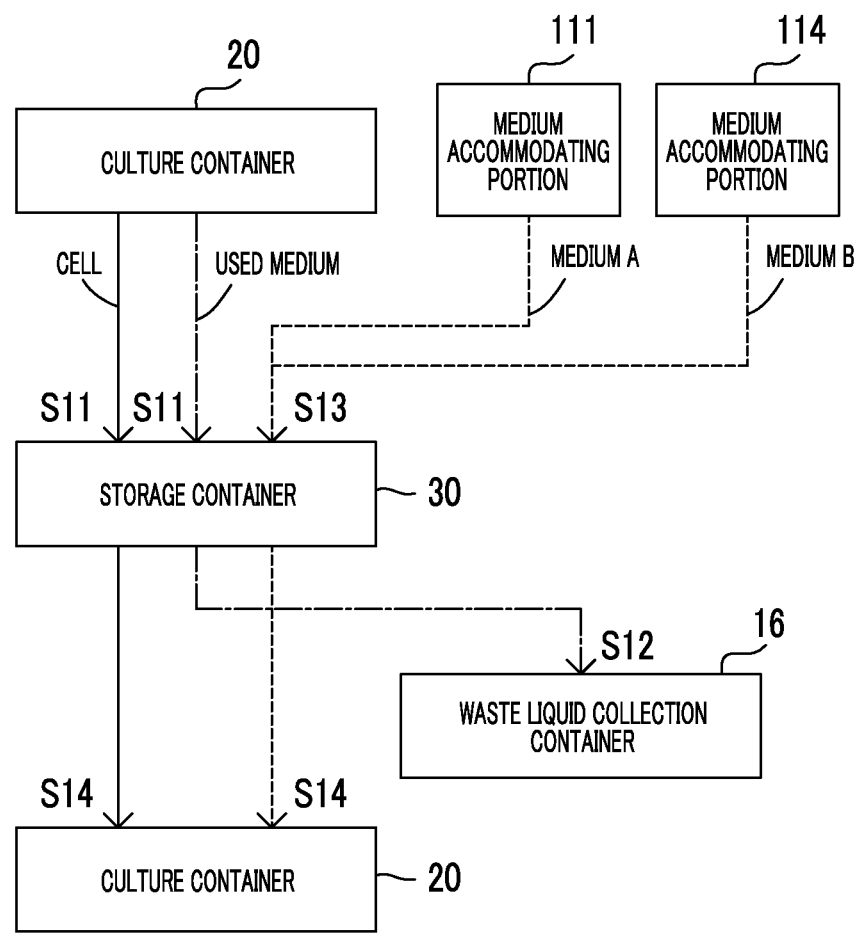
FIG. 3 is a view showing a flow of cells or the like in a case of performing a medium exchange process in the cell culture device according to the first embodiment of the present invention.

In a cell culture, a medium is deteriorated due to metabolites secreted from the cells. For this reason, a medium exchange process of exchanging a used medium in the culture container 20 with a new medium at an appropriate timing within the culture period is required. The cell culture device 10 according to the present embodiment performs the above-described medium exchange process as follows. FIG. 3 is a view showing a flow of cells, media, and the like in a case where the cell culture device 10 performs a medium exchange process. A correspondence between the flow of cells, media, and the like and each processing step shown below is shown in FIG. 3.

In Step S11, the on-off valves V12, V15, and V13 are made to enter an open state. In addition, the atmosphere within the culture container 20 is pressurized by the pressure adjustment mechanism 26. Accordingly, cells and the used medium which have been accommodated in the culture container 20 flow out into the circulation flow path F1 and are transferred into the storage container 30.

In Step S12, a concentration process in which the used medium is removed from a mixture containing the cells and the used medium which have been stored in the storage container 30 is performed. The concentration process is performed in the same procedure as that of the process in Step S2 of the above-described subculture process. The used medium is collected in the waste liquid collection container 16 through the concentration process and the cells stay in the pipe a5. Diluent may be introduced into the storage container 30 in order to promote precipitation of the cells.

In Step S13, the on-off valves V2, V3, and V6 are made to enter an open state and the pumps P2 and P3 are driven. Accordingly, a new medium A and a new medium B which have been accommodated in the medium accommodating portions 111 and 114 flow into the storage container 30 via the flow path F3 and the circulation flow path F1. Thereafter, the on-off valve V14 is made to enter an open state, and a new medium containing the medium A and the medium B flows out from the storage container 30 and joins to the cells staying in the pipe a5.

In Step S14, the on-off valves V14, V16, and V11 are made to enter an open state. In addition, the atmosphere within the storage container 30 is pressurized by the pressure adjustment mechanism 33. Accordingly, the cells and the new medium which have been staying in the pipe a5 flow into the culture container 20. The cells accommodated in the culture container 20 are cultured using the new medium. The medium exchange process is completed through the process of the above-described Steps S11 to S14.

<Division Process (Mechanical Division Process)>

Figure 4:
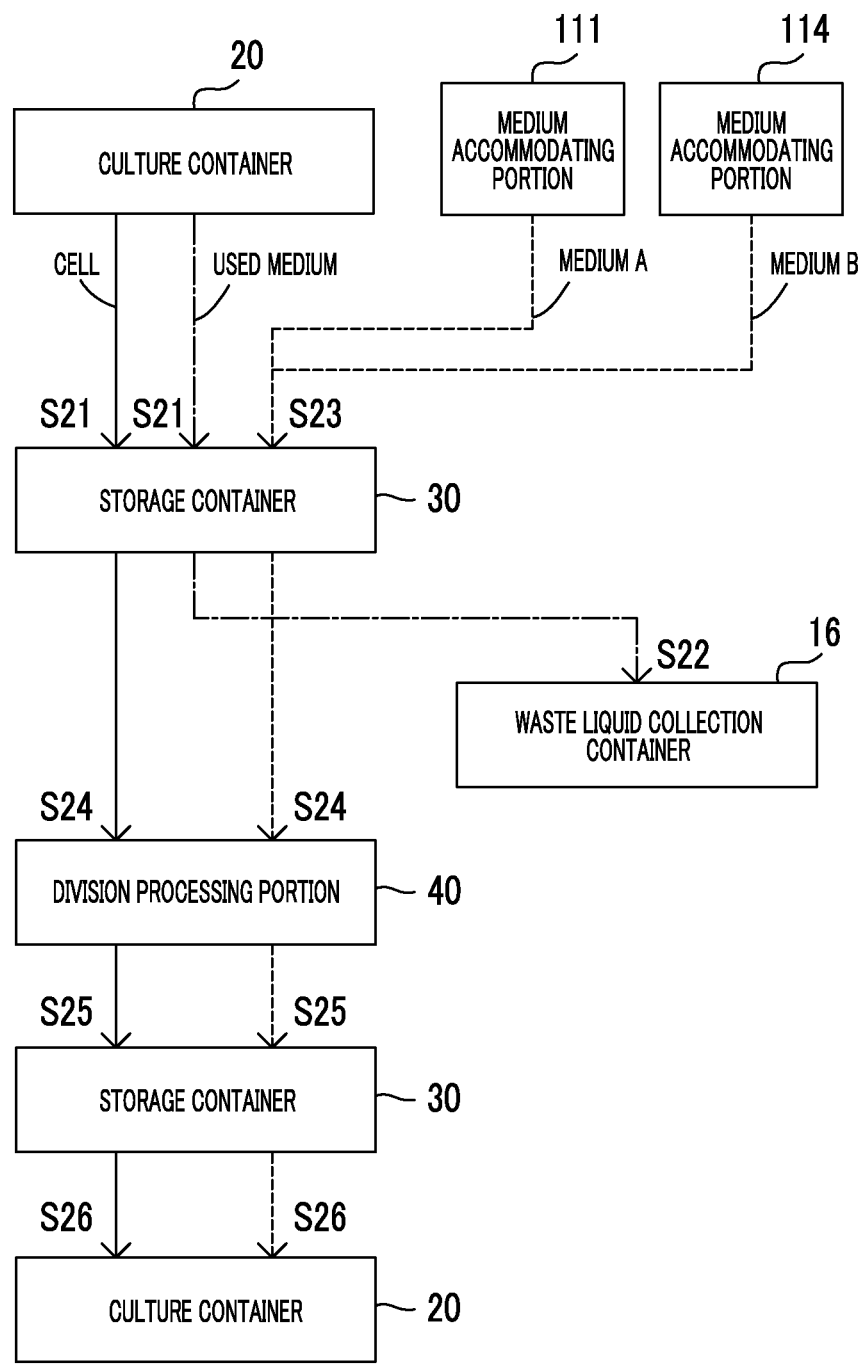
FIG. 4 is a view showing a flow of cells or the like in a case of performing a division process in the cell culture device according to the first embodiment of the present invention.

During the culture of, for example, pluripotent stem cells, problems may arise such that cells start to differentiate due to an adhesive fusion of cell aggregations (spheres), which have been generated through the culture of cells, if the sizes of the cell aggregations become too large, or such that cells in a central portion of a cell aggregation necrose. Accordingly, in some cases, a division process in which a cell aggregation is divided at an appropriate timing during a culture period is necessary in order to prevent the size of the cell aggregation from becoming too large. The cell culture device 10 according to the present embodiment performs the above-described division process as follows. In the following description, a case where the division process in the division processing portion 40 is a mechanical division process, will be exemplified. FIG. 4 is a view showing a flow of cells, media, and the like in a case where the cell culture device 10 performs a division process. A correspondence between the flow of cells, media, and the like and each processing step shown below is shown in FIG. 4.

In Step S21, the on-off valves V12, V15, and V13 are made to enter an open state. In addition, the atmosphere within the culture container 20 is pressurized by the pressure adjustment mechanism 26. Cell aggregations generated in the culture container 20 and a used medium flow out into the circulation flow path F1 and are transferred into the storage container 30.

In Step S22, a concentration process in which the used medium is removed from a mixture containing the cell aggregations and the used medium which have been stored in the storage container 30 is performed. The concentration process is performed in the same procedure as that of the process in Step S2 of the above-described subculture process. The used medium is collected in the waste liquid collection container 16 through the concentration process and the cell aggregations stay in the pipe a5. A diluent may be introduced into the storage container 30 in order to promote precipitation of the cells.

In Step S23, the on-off valves V2, V3, and V6 are made to enter an open state and the pumps P2 and P3 are driven. Accordingly, a new medium A and a new medium B which have been accommodated in the medium accommodating portions 111 and 114 flow into the storage container 30 via the flow path F3 and the circulation flow path F1. Thereafter, the on-off valve V14 is made to enter an open state, and a new medium containing the medium A and the medium B flows out from the storage container 30 and joins to the cell aggregations staying in the pipe a5.

In Step S24, the on-off valves V14, V16, and V21 are made to enter an open state. In addition, the atmosphere within the storage container 30 is pressurized by the pressure adjustment mechanism 33. Accordingly, the cell aggregations and the medium which have been staying in the pipe a5 flow into the flow path F2 via the connection region X1 and flow into the division processing portion 40. The cells flowing into the division processing portion 40 are subjected to a division process within the processing container 42.

In Step S25, the on-off valves V22 and V13 are made to enter an open state. In addition, the atmosphere within the pressure container 41 and the processing container 42 is pressurized by the pressure adjustment mechanism 43. Accordingly, the cells which have been subjected to the division process flow out into the circulation flow path F1 via the connection region X2 together with the medium and are transferred into the storage container 30.

In Step S26, the on-off valves V14, V16, and V11 are made to enter an open state. In addition, the atmosphere within the storage container 30 is pressurized by the pressure adjustment mechanism 33. Accordingly, the cells and the new medium which have been stored in the storage container 30 and subjected to the division process flow into the culture container 20. Culturing of the cells subjected to the division process is continuously performed within the culture container 20. The division process is completed through the process of the above-described Steps S21 to S26.

In the above-described example, the concentration process and the supply of a new medium are performed before the division process. However, the concentration process and the supply of a new medium may be performed after the division process.

<Division Process (Enzymatic Process)>

Figure 5:
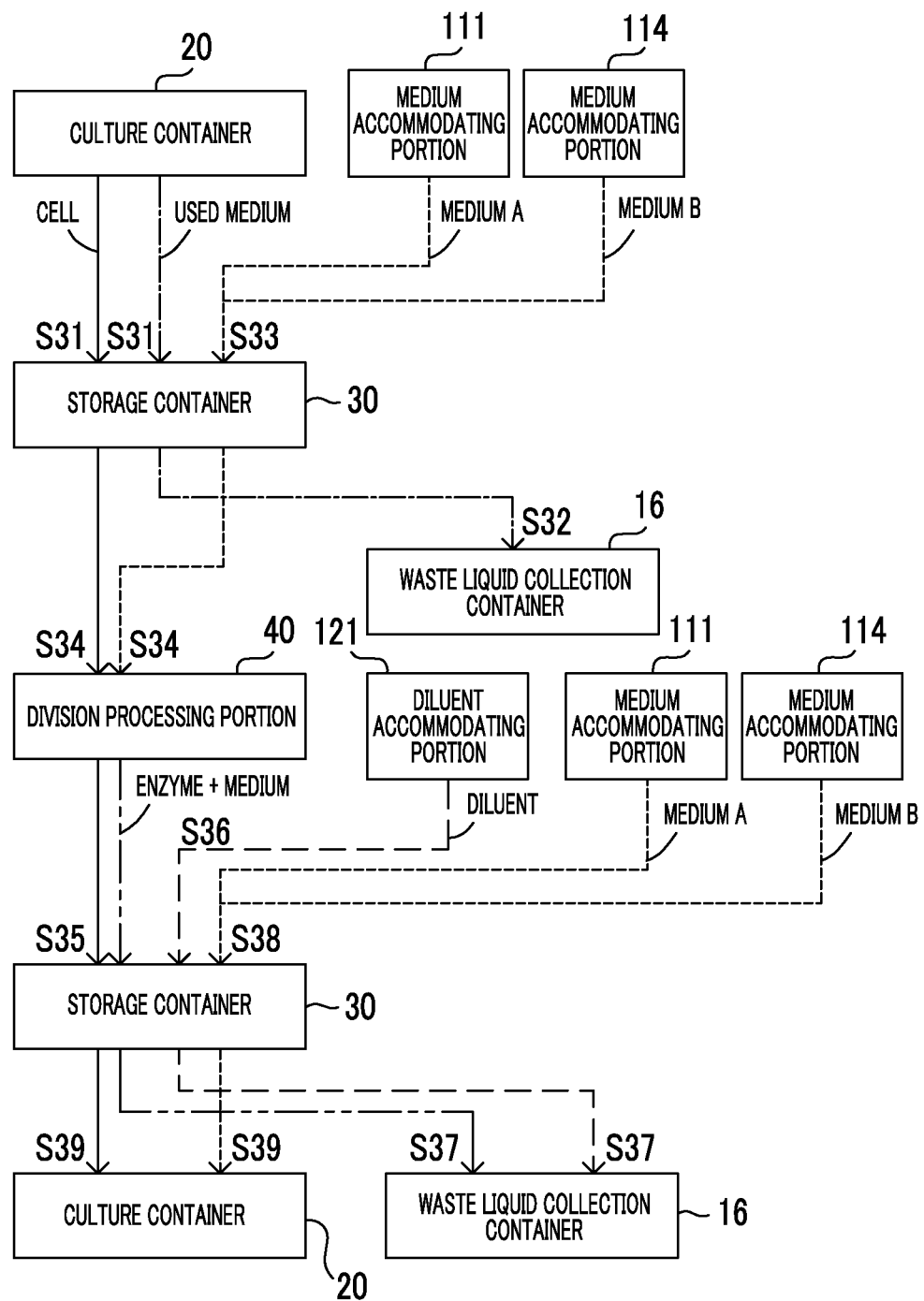
FIG. 5 is a view showing a flow of cells or the like in a case of performing a division process in the cell culture device according to the first embodiment of the present invention.

FIG. 5 is a view showing a flow of cells, media, and the like in a case where the cell culture device 10 performs a division process in the division processing portion 40 which includes an enzymatic process in which the above-described cell dissociation enzyme is used. A correspondence between the flow of cells, media, and the like and each processing step shown below is shown in FIG. 5.

The process of Steps S31 to S33 in FIG. 5 is the same as the process of the above-described Steps S21 to S23, and therefore, the description thereof will not be repeated.

In Step S34, the on-off valves V14, V16, and V21 are made to enter an open state. In addition, the atmosphere within the storage container 30 is pressurized by the pressure adjustment mechanism 33. Accordingly, the cell aggregations and the medium which have been staying in the pipe a5 flow into the flow path F2 via the connection region X1 and flow into the division processing portion 40. The cells flowing into the division processing portion 40 are subjected to a division process, in which a cell dissociation enzyme is used, within the processing container 42.

In Step S35, the on-off valves V22 and V13 are made to enter an open state. In addition, the atmosphere within the pressure container 41 and the processing container 42 is pressurized by the pressure adjustment mechanism 43. Accordingly, the cells subjected to the division process flow out into the circulation flow path F1 via the connection region X2 together with a medium containing a cell dissociation enzyme, and are transferred into the storage container 30.

In Step S36, the on-off valves V4 and V6 are made to enter an open state and the pump P4 is driven. Accordingly, the diluent accommodated in the diluent accommodating portion 121 flows into the storage container 30 via the flow path F3 and the circulation flow path F1. A cell dissociation action using the cell dissociation enzyme is stopped by adding the diluent to the cells and the medium containing the cell dissociation enzyme, the cells and the medium being accommodated in the storage container 30.

In Step S37, a concentration process of removing the diluent and the medium containing the cell dissociation enzyme from a mixture which contains the cells, the medium containing the cell dissociation enzyme, and the diluent and is stored in the storage container 30, is performed. The concentration process is performed in the same procedure as that of the process in Step S2 of the above-described subculture process. The medium containing the cell dissociation enzyme and the diluent are collected in the waste liquid collection container 16 through the concentration process and the cells stay in the pipe a5.

In Step S38, the on-off valves V2, V3, and V6 are made to enter an open state and the pumps P2 and P3 are driven. Accordingly, a new medium A and a new medium B which have been accommodated in the medium accommodating portions 111 and 114 flow into the storage container 30 via the flow path F3 and the circulation flow path F1. Thereafter, the on-off valve V14 is made to enter an open state, and a new medium containing the medium A and the medium B flows out from the storage container 30 and joins to the cells staying in the pipe a5.

In Step S39, the on-off valves V14, V16, and V11 are made to enter an open state. In addition, the atmosphere within the storage container 30 is pressurized by the pressure adjustment mechanism 33. Accordingly, the cells, which have stayed in the pipe a5 and have been subjected to the division process, and the new medium flow into the culture container 20. Culturing of the cells subjected to the division process is continuously performed within the culture container 20. The division process is completed through the process of the above-described Steps S31 to S39.

In the above-described example, the concentration process and the supply of a new medium are performed before the division process. However, the concentration process and the supply of a new medium may be performed after the division process.

<Freezing Process>

Figure 6:
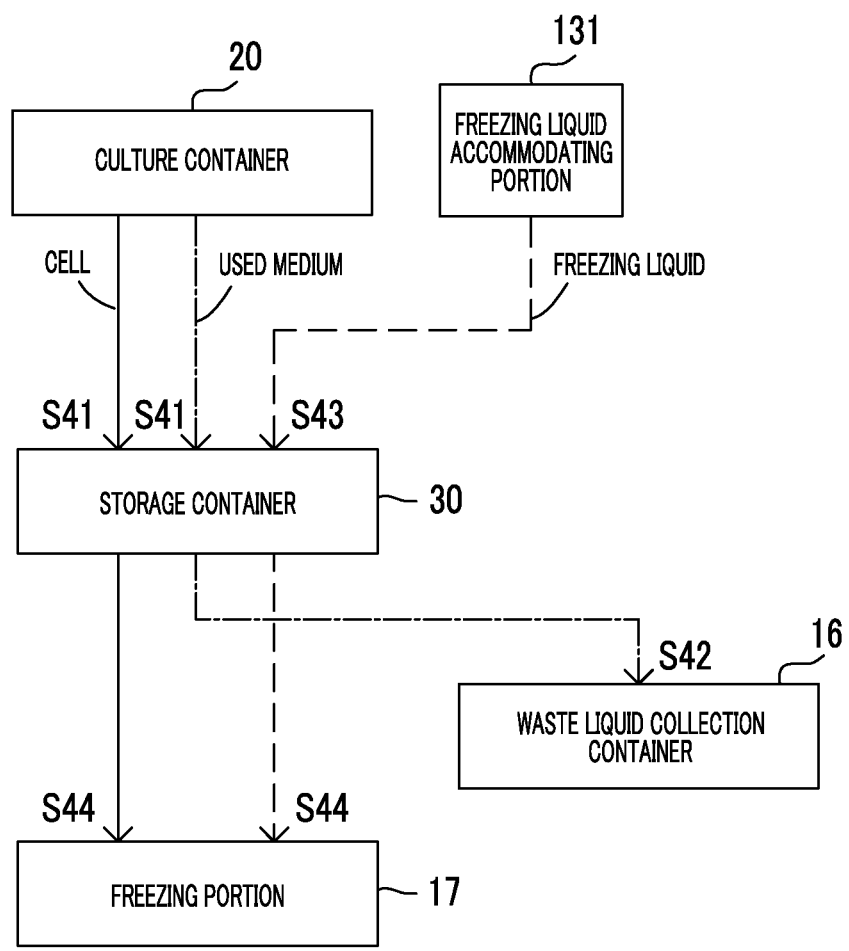
FIG. 6 is a view showing a flow of cells or the like in a case of performing a freezing process in the cell culture device according to the first embodiment of the present invention.

In a case of preservation after collecting the cells which have been cultured, cells are generally collected in a preservation container for cryopreservation. The cell culture device 10 according to the present embodiment performs a freezing process, in which cultured cells are collected and frozen, as follows. FIG. 6 is a view showing a flow of cells, media, and the like in a case where the cell culture device 10 performs a freezing process. A correspondence between the flow of cells, media, and the like and each processing step shown below is shown in FIG. 6.

In Step S41, the on-off valves V12, V15, and V13 are made to enter an open state. In addition, the atmosphere within the culture container 20 is pressurized by the pressure adjustment mechanism 26. Accordingly, cells and a used medium which have been accommodated in the culture container 20 flow out into the circulation flow path F1 and are transferred into the storage container 30.

In Step S42, a concentration process in which the used medium is removed from a mixture containing the cells and the used medium which have been stored in the storage container 30 is performed. The concentration process is performed in the same procedure as that of the process in Step S2 of the above-described subculture process. The used medium is collected in the waste liquid collection container 16 through the concentration process and the cells stay in the pipe a5. Diluent may be introduced into the storage container 30 in order to promote precipitation of the cells.

In Step S43, the on-off valves V5 and V6 are made to enter an open state and the pump P5 is driven. Accordingly, a freezing liquid accommodated in the freezing liquid accommodating portion 131 flows into the storage container 30 via the flow path F3 and the circulation flow path F1. Thereafter, the on-off valve V14 is made to enter an open state, and the freezing liquid flows out from the storage container 30 and joins to the cells staying in the pipe a5.

In Step S44, the on-off valves V14, V16, and V41 are made to enter an open state. In addition, the atmosphere within the storage container 30 is pressurized by the pressure adjustment mechanism 33. Accordingly, the cells and the freezing liquid which have been staying in the pipe a5 are accommodated in the preservation container 17a of the freezing portion 17 via the flow path F5. The freezing portion 17 freezes the cells accommodated in the preservation container 17a together with the freezing liquid. The freezing process is completed through the process of the above-described Steps S41 to S44.

A method disclosed, for example, in JP4705473B may be applied as the method for cryopreserving cells. This method includes a step of quickly freezing the cells in a medium containing dimethyl sulfoxide (DMSO), propylene glycol, acetamide, and a medium in predetermined amounts. In addition, a method disclosed in JP4223961B may be applied. This method is a method for cryopreserving cells using a cryopreservation liquid containing at least one selected from the group consisting of dimethyl sulfoxide, glycerin, ethylene glycol, propylene glycol, and polyvinyl pyrrolidone as a cryoprotective agent at a predetermined concentration, and includes a step of suspending the cells in a cryopreservation liquid, a cooling step of cooling and freezing the cryopreservation liquid up to $-80°$ C. or lower at a predetermined cooling rate, and a preservation step of preserving the cryopreservation liquid at $-80°$ C. or lower.

In the subculture process, the medium exchange process, and the division process described above, a case of supplying two types of media A and B from the medium supply portion 110 has been exemplified. However, the type of medium to be used can be appropriately changed in accordance with a cell culture protocol. That is, the type of medium to be used may be one or may be greater than or equal to three in accordance with a culture protocol.

<Cell Culture Process>

Figure 7:
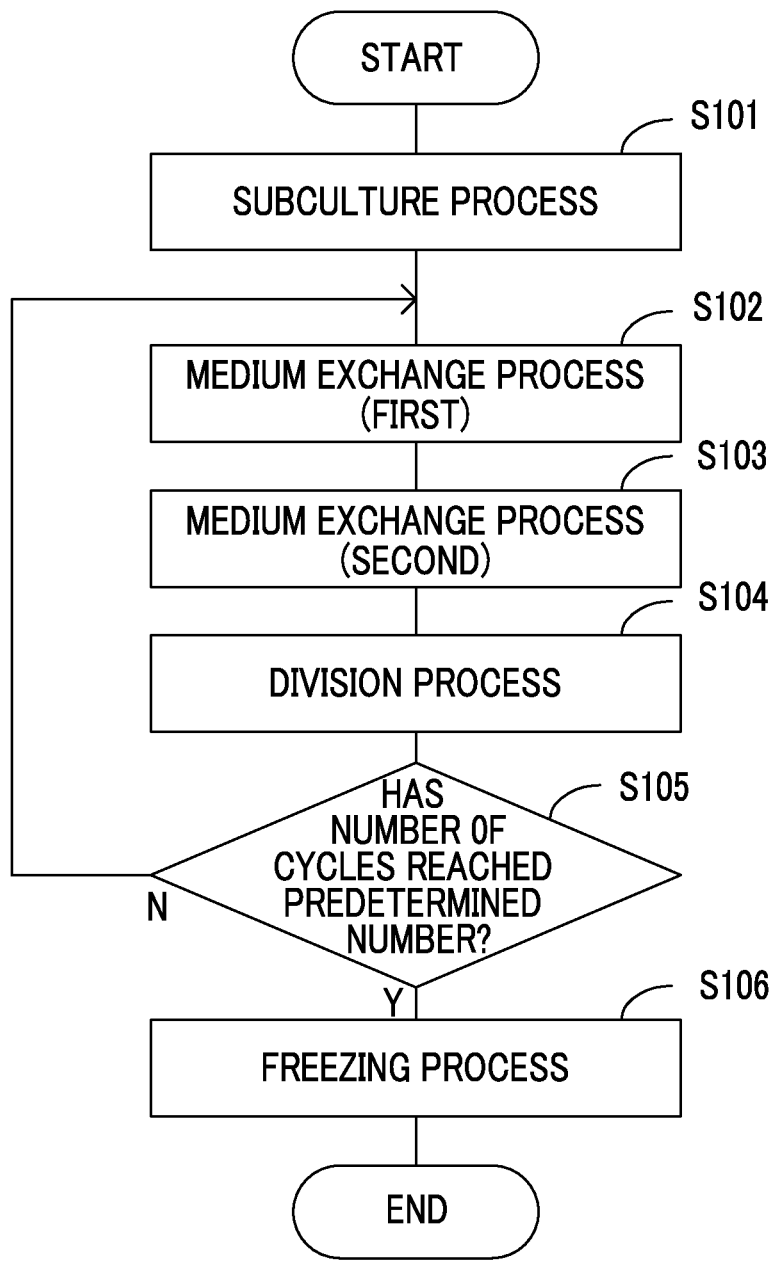
FIG. 7 is a flowchart showing an example of a cell culture method in which the cell culture device according to the embodiment of the present invention is used.

The cell culture device 10 can automatically perform cell culture without human intervention using the control portion 18 performing a cell culture processing program exemplified below. FIG. 7 is a flowchart showing a flow of a process of the cell culture program executed by the control portion 18.

In Step S101, the control portion 18 performs the above-described subculture process to start cell culture by accommodating cells supplied from the cell supply portion 100 and a medium supplied from the medium supply portion 110 in the culture container 20.

In Step S102, the control portion 18 performs the above-described medium exchange process (first time) after a predetermined period of time has elapsed since the start of the cell culture to continue the cell culture by exchanging the used medium within the culture container 20 with new media accommodated in the medium accommodating portions 111 and 114.

In Step S103, the control portion 18 performs the above-described medium exchange process (second time) after a predetermined period of time has elapsed since performing the first medium exchange process to continue the cell culture by exchanging the used medium within the culture container 20 with new media accommodated in the medium accommodating portions 111 and 114.

In Step S104, the control portion 18 performs the above-described division process after a predetermined period of time has elapsed since performing the second medium exchange process to continue the cell culture by dividing a cell aggregation.

In Step S105, the control portion 18 determines whether or not the number of culture cycles, in which the process in the above-described Steps S102 to S104 is regarded as one cycle, has reached a predetermined number. In a case where it is determined that the number of culture cycles has not reached the predetermined number, the control portion 18 returns the process back to Step S102. In contrast, in a case where it is determined that the number of culture cycles has reached the predetermined number, the control portion 18 advances the process to Step S106. The scale of the cell culture is increased in accordance with the progress of the culture cycles.

In Step S106, the control portion 18 performs the above-described freezing process to perform cryopreservation by accommodating the cultured cells in the preservation container 17a of the freezing portion 17.

In the above-described example, the medium exchange process has been performed twice within one culture cycle. However, the number of times of performing the medium exchange process within one culture cycle can be appropriately changed.

As is clear from the above-described description, the cell culture device 10 according to the present embodiment has the circulation flow path F1 connecting the inflow port 21 to the outflow port 22 of the culture container 20. In addition, the cell culture device 10 has the storage container 30 provided inside the circulation flow path F1. The storage container 30 has the inflow port 31 connected to the outflow port 22 of the culture container 20 and the outflow port 32 connected to the inflow port 21 of the culture container 20. The storage container 30 is provided for the concentration process or the like performed in the subculture process, the medium exchange process, the division process, and the freezing process described above. In addition, the cell culture device 10 has the flow path F2 connecting the connection region X1 within the circulation flow path F1 positioned between the outflow port 32 of the storage container 30 and the inflow port 21 of the culture container 20 to the connection region X2 within the circulation flow path F1 positioned between the inflow port 31 of the storage container 30 and the outflow port 22 of the culture container 20. The cell culture device 10 has the division processing portion 40 which is provided within the flow path F2, divides a cell aggregation flowing in from the circulation flow path F1 via the connection region X1, and allowing the divided cell aggregation to flow out into the circulation flow path F1 via the connection region X2. In addition, the cell culture device 10 has the medium supply portion 110 supplying a medium to the inside of the circulation flow path F1.

By forming the cell culture device 10 as described above, it is possible to continuously perform a series of processes, such as a medium exchange process or a division process, which are required for cell culture in a closed system. Accordingly, it is possible to produce a large amount of homogeneous cells. According to the cell culture device 10 of the present embodiment, it is possible to perform a series of processes from a subculture process to a freezing process which are required for cell culture without human intervention.

In addition, according to the cell culture device 10 of the present embodiment, the transfer of cells into the storage container 30 from the culture container 20, the transfer of cells to the division processing portion 40 and the culture container 20 from the storage container 30, and the transfer of cells to the storage container 30 from the division processing portion 40 are all performed through feeding pressure using the pressure adjustment mechanisms 26, 33, and 43. Accordingly, it is possible to reduce the damage to the cells as compared to a case of transferring the cells using liquid contact pumps such as a diaphragm pump, a tube pump, a peristaltic pump, and a Mohno pump, and therefore, it is possible to suppress the decrease in cell viability. In the cell culture device 10 according to the present embodiment, a case where the process from the subculture process to the freezing process is automated using the control portion 18 controlling the operation of the on-off valves V1 to V5, V11 to V16, V21, V22, V31, and V41, pumps P1 to P5, and the pressure adjustment mechanisms 26, 33, and 43 has been exemplified, but the present invention is not limited to this aspect. The on-off valves V1 to V5, V11 to V16, V21, V22, V31, and V41, the pumps P1 to P5, and the pressure adjustment mechanisms 26, 33, and 43 may be manually operated by a user.

[Second Embodiment]

Figure 8:
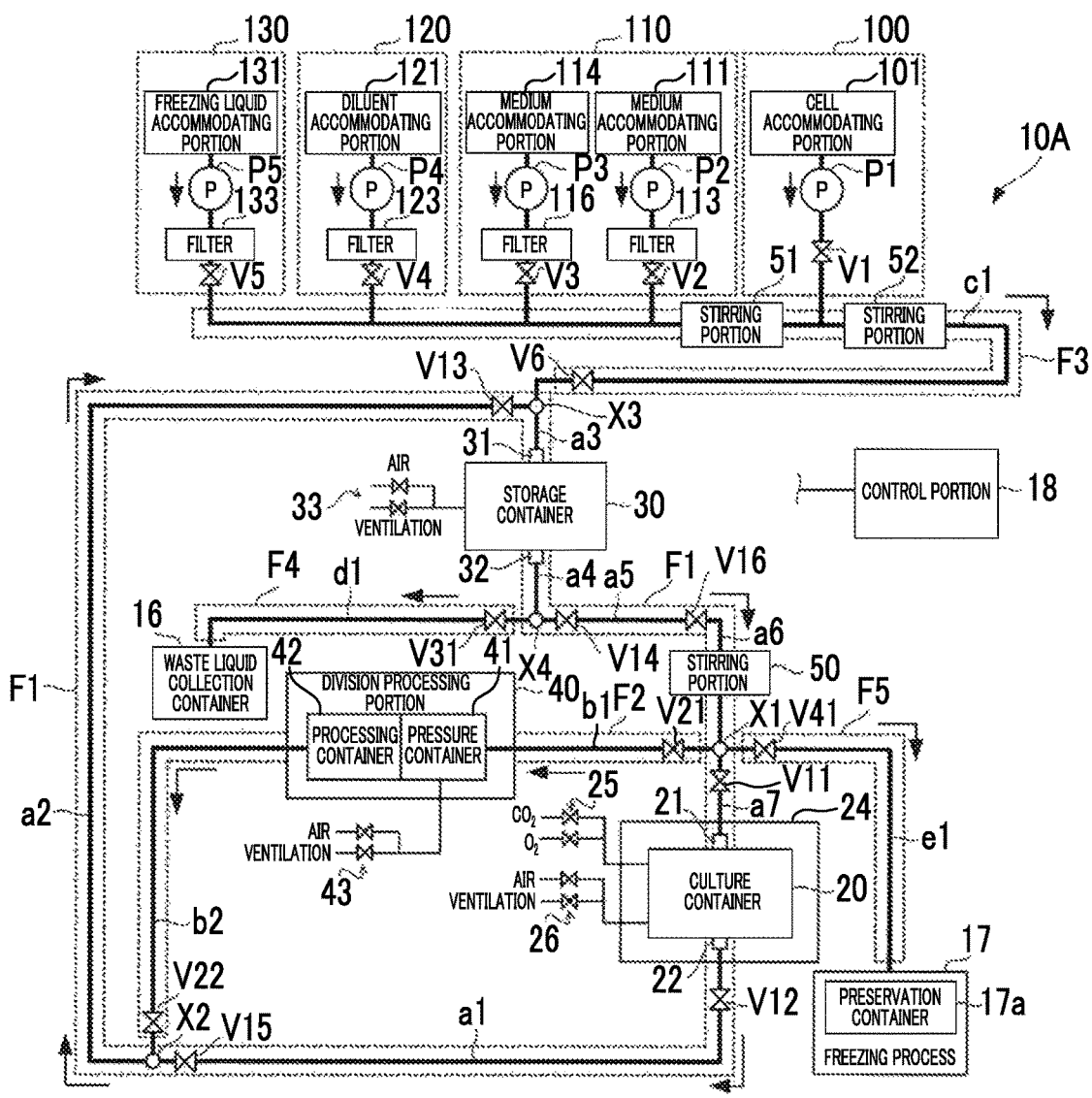
FIG. 8 is a view showing a configuration of a cell culture device according to a second embodiment of the present invention.

FIG. 8 is a view showing a configuration of a cell culture device 10A according to a second embodiment of the present invention. The cell culture device 10A has a configuration in which stirring portions 50, 51, and 52 are added to the cell culture device 10 according to the first embodiment described above. The stirring portions 50, 51, and 52 have a function of stirring a fluid flowing in. The stirring portions 50, 51, and 52 preferably have a configuration without a driving portion as a so-called static mixer, and can include, for example, a tubular body and a stirring element which is installed so as to be fixed inside the tubular body and forms a helical flow path inside the tubular body. The flow path inside the tubular body constituting the static mixer does not necessarily have a helical shape. The static mixer may have a structure in which a plate-like member forming the flow path inside the tubular body is appropriately disposed inside the tubular body or a structure in which the inner diameter of the tubular body is partially changed, so as to stir a fluid passing through the inside of the tubular body.

The stirring portion 50 is provided between the outflow port 32 of the storage container 30 and the inflow port 21 of the culture container 20 within the circulation flow path F1. More specifically, the stirring portion 50 is provided between the outflow port 32 of the storage container 30 and the connection region X1 within the circulation flow path F1. The stirring portion 50 may be provided between the connection region X1 and the inflow port 21 of the culture container 20 within the circulation flow path F1. The stirring portion 51 is provided between the medium supply portion 110 and the cell supply portion 100 within the flow path F3. In contrast, the stirring portion 52 is provided on a downstream side of a region, to which a pipe from the cell supply portion 100 is connected, in the flow path F3.

The stirring portion 50 is an example of a first stirring portion in the present invention. The stirring portion 51 is an example of a second stirring portion in the present invention. The stirring portion 52 is an example of a third stirring portion in the present invention.

Hereinafter, a subculture process, a medium exchange process, a division process, and a freezing process which can be performed in the cell culture device 10A according to the second embodiment will be described. The subculture process, the medium exchange process, the division process, and the freezing process described below are realized using the control portion 18 controlling the operation of the on-off valves V1 to V5, V11 to V16, V21, V22, V31, and V41, pumps P1 to P5, and the pressure adjustment mechanisms 26, 33, and 43.

<Subculture Process>

Figure 9:
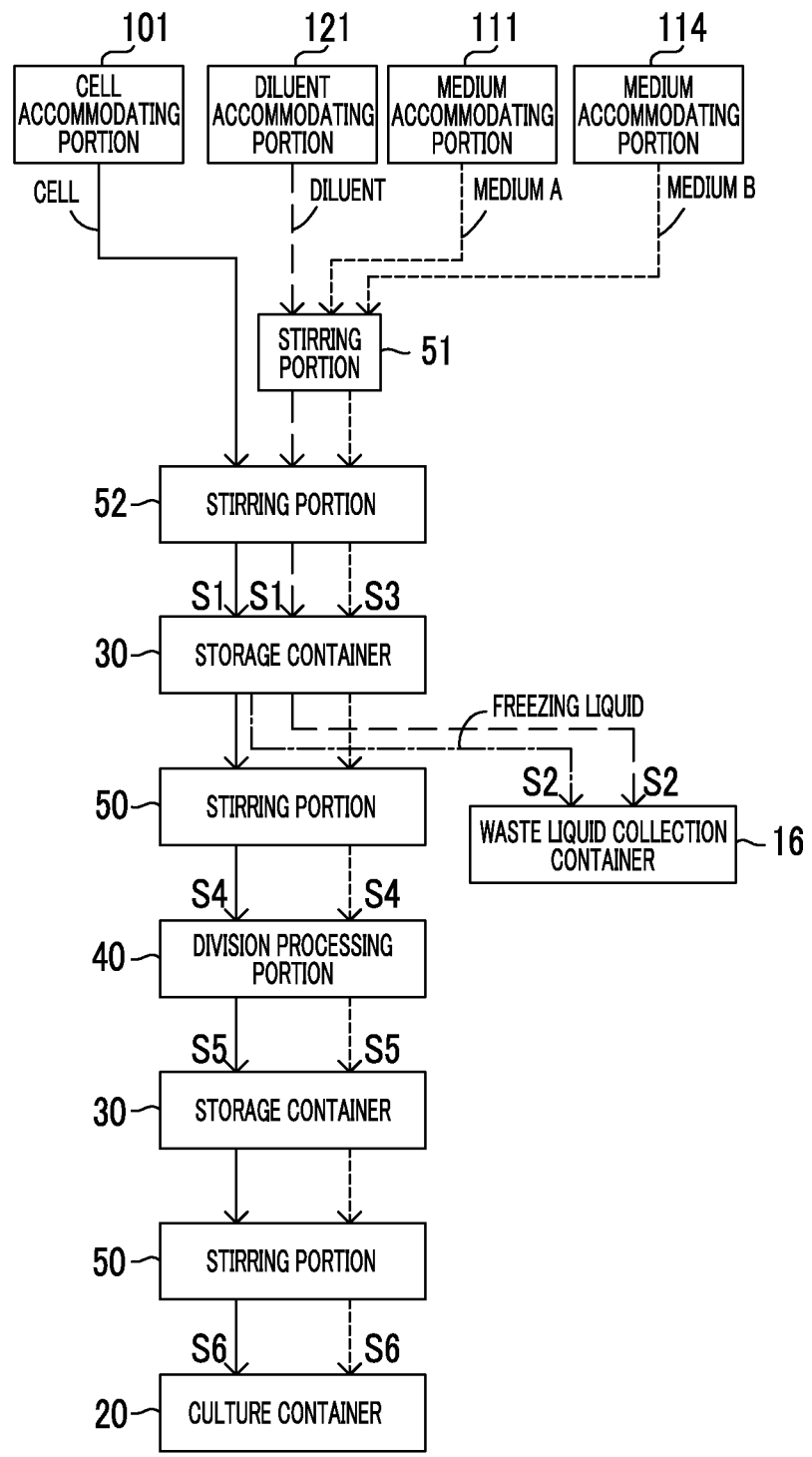
FIG. 9 is a view showing a flow of cells or the like in a case of performing a subculture process in the cell culture device according to the second embodiment of the present invention.

Hereinafter, a subculture process using the cell culture device 10A according to the second embodiment will be described. In the following description, a case where a division process in the division processing portion 40 is a mechanical division process will be exemplified. In addition, in the following description, matters overlapping with the subculture process according to the first embodiment will be appropriately omitted. FIG. 9 is a view showing a flow of cells, media, and the like in a case where the cell culture device 10A performs a subculture process, and corresponds to FIG. 2 according to the first embodiment. A correspondence between the flow of cells, media, and the like and each processing step shown below is shown in FIG. 9.

In Step S1, cells accommodated in the cell accommodating portion 101 in a frozen state and diluent accommodated in the diluent accommodating portion 121 flow into the storage container 30 via the flow path F3 and the circulation flow path F1. The cells and the diluent are stirred and mixed with each other by passing through the stirring portion 52 within the flow path F3.

In Step S2, a concentration process in which a freezing liquid and diluent are removed from a mixture which contains the cells, the freezing liquid, and the diluent and is stored in the storage container 30, the freezing liquid and the diluent accompanying the cells, is performed. The freezing liquid and the diluent are collected in the waste liquid collection container 16 through the concentration process, and the cells stay within the pipe a5.

In Step S3, a medium A and a medium B which have been accommodated in the medium accommodating portions 111 and 114 flow into the storage container 30 via the flow path F3 and the circulation flow path F1. The medium A and the medium B pass through the stirring portions 51 and 52 within the flow path F3. The medium A and the medium B are stirred and mixed with each other by passing through the stirring portions 51 and 52. In the floating culture, a case where the medium A and the medium B have a viscosity difference from each other is assumed. By stirring the medium A and the medium B using the stirring portions 51 and 52, a mixed medium with a homogeneous viscosity can be obtained before being mixed with the cells. Thereafter, the on-off valve V14 is made to enter an open state, and the mixed medium containing the medium A and the medium B flows out from the storage container 30 and joins to the cells staying in the pipe a5.

In Step S4, the cells and the medium which have been staying in the pipe a5 are transferred into the division processing portion 40. The cells flowing into the division processing portion 40 are subjected to a division process within the processing container 42. Accordingly, the cells in a frozen state are divided. In Step S5, the cells subjected to the division process are transferred into the storage container 30 together with the medium.

In Step S6, the cells and the medium which have been stored in the storage container 30 flow into the culture container 20 via the stirring portion 50. The cells and the medium are stirred and mixed with each other by passing through the stirring portion 50. Accordingly, the distance between the cells floating in the medium becomes uniform.

In this manner, according to the subculture process using the cell culture device 10A of the present embodiment, cells which have been supplied from the cell supply portion 100 are accommodated in the culture container 20 in a state where the distance between the cells in the medium becomes uniform. In the above-described example, the concentration process and the supply of a new medium are performed before the division process. However, the concentration process and the supply of a new medium may be performed after the division process.

<Medium Exchange Process>

Figure 10:
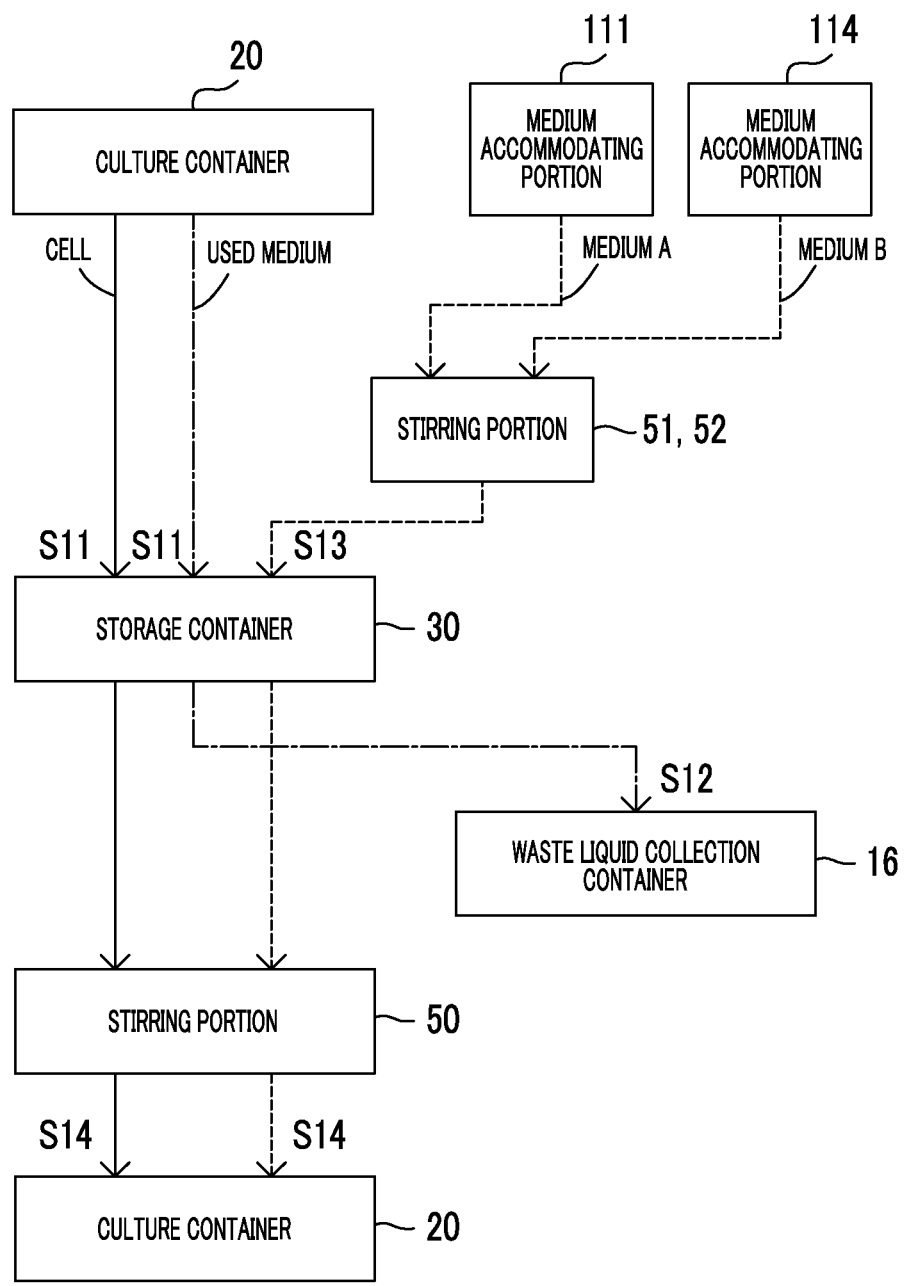
FIG. 10 is a view showing a flow of cells or the like in a case of performing a medium exchange process in the cell culture device according to the second embodiment of the present invention.

Hereinafter, a medium exchange process using the cell culture device 10A according to the second embodiment will be described. In the following description, matters overlapping with the medium exchange process according to the first embodiment will be appropriately omitted. FIG. 10 is a view showing a flow of cells, media, and the like in a case where the cell culture device 10A performs a medium exchange process, and corresponds to FIG. 3 according to the first embodiment. A correspondence between the flow of cells, media, and the like and each processing step shown below is shown in FIG. 10.

In Step S11, the cells and a used medium are transferred into the storage container 30 from the culture container 20. In Step S12, a concentration process in which the used medium is removed from a mixture containing the cells and the used medium which have been stored in the storage container 30 is performed. The used medium is collected in the waste liquid collection container 16 through the concentration process and the cells stay in the pipe a5.

In Step S13, a new medium A and a new medium B which have been accommodated in the medium accommodating portions 111 and 114 flow into the storage container 30 via the flow path F3 and the circulation flow path F1. The medium A and the medium B pass through the stirring portions 51 and 52 within the flow path F3. The medium A and the medium B are stirred and mixed with each other by passing through the stirring portions 51 and 52. Thereafter, the on-off valve V14 is made to enter an open state and the new medium containing the medium A and the medium B flows out from the storage container 30 and joins to the cells staying in the pipe a5.

In Step S14, the cells and the new medium which have been staying in the pipe a5 flow into the culture container 20 via the stirring portion 50. The cells and the new medium are stirred and mixed with each other by passing through the stirring portion 50. Accordingly, the distance between the cells floating in the medium becomes uniform. In this manner, according to the medium exchange process using the cell culture device 10A according to the present embodiment, the cells taken out from the culture container 20 are returned to the inside of the culture container 20 in a state where the distance between the cells within the new medium becomes uniform.

<Division Process>

Figure 11:
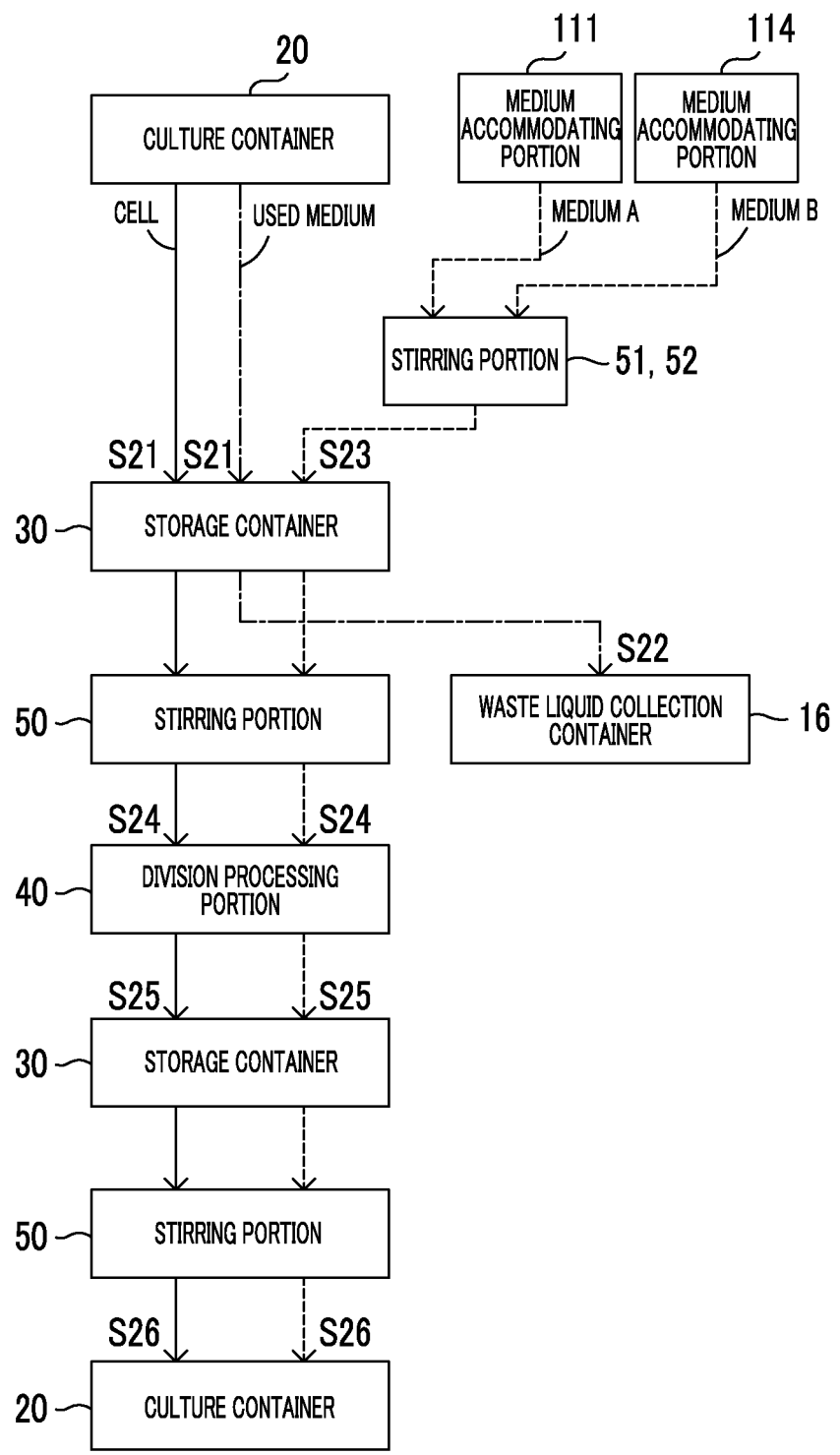
FIG. 11 is a view showing a flow of cells or the like in a case of performing a division process in the cell culture device according to the second embodiment of the present invention.

Hereinafter, a division process using the cell culture device 10A according to the second embodiment will be described. In the following description, a case where a division process in the division processing portion 40 is a mechanical division process will be exemplified. In addition, in the following description, matters overlapping with the division process according to the first embodiment will be appropriately omitted. FIG. 11 is a view showing a flow of cells, media, and the like in a case where the cell culture device 10A performs a division process, and corresponds to FIG. 4 according to the first embodiment. A correspondence between the flow of cells, media, and the like and each processing step shown below is shown in FIG. 11.

In Step S21, the cells and a used medium are transferred into the storage container 30 from the culture container 20. In Step S22, a concentration process in which the used medium is removed from a mixture containing the cells and the used medium which have been stored in the storage container 30 is performed. The used medium is collected in the waste liquid collection container 16 through the concentration process and the cells stay in the pipe a5.

In Step S23, a new medium A and a new medium B which have been accommodated in the medium accommodating portions 111 and 114 flow into the storage container 30 from the inflow port 31 via the flow path F3 and the circulation flow path F1. The medium A and the medium B are stirred and mixed with each other by passing through the stirring portions 51 and 52 within the flow path F3. Thereafter, the on-off valve V14 is made to enter an open state and the new medium containing the medium A and the medium B flows out from the storage container 30 and joins to the cells staying in the pipe a5.

In Step S24, the cells and the new medium which have been staying in the pipe a5 are transferred into the division processing portion 40, and a division process is performed on the cell aggregations within the division processing portion 40. In Step S25, the cells subjected to the division process are transferred into the storage container 30 together with the medium.

In Step S26, the cells and the medium which have been stored in the storage container 30 flow into the culture container 20 from the inflow port 21 via the stirring portion 50. The cells and the medium are stirred and mixed with each other by passing through the stirring portion 50. Accordingly, the distance between the cells floating in the medium becomes uniform.

In this manner, according to the division process using the cell culture device 10A of the present embodiment, the cells which have been taken out from the culture container 20 are subjected to the division process, and are returned to the culture container 20 in a state where the distance between the cells in a new medium becomes uniform. In the above-described example, the concentration process and the supply of a new medium are performed before the division process. However, the concentration process and the supply of a new medium may be performed after the division process.

<Freezing Process>

Figure 12:
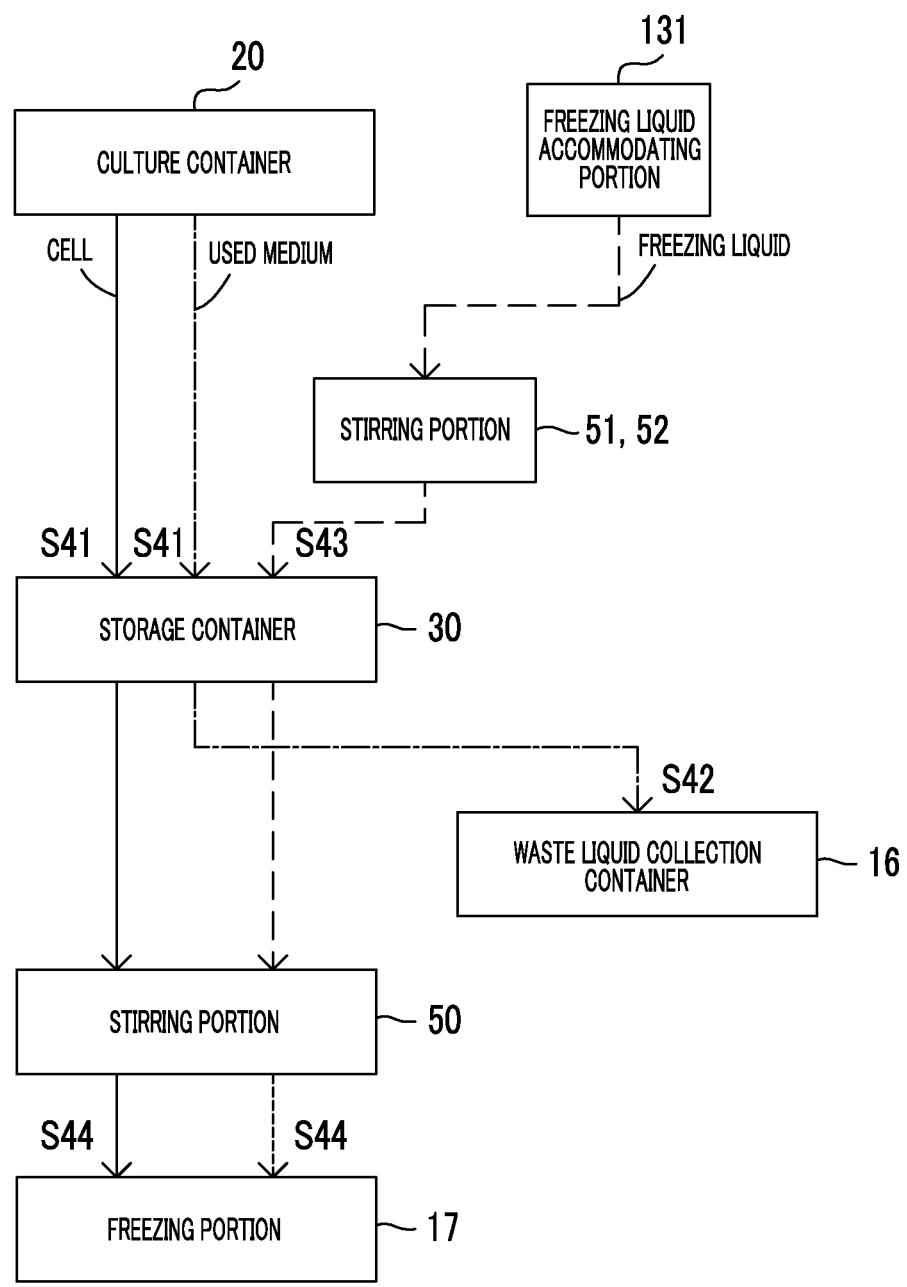
FIG. 12 is a view showing a flow of cells or the like in a case of performing a freezing process in the cell culture device according to the second embodiment of the present invention.

Hereinafter, a freezing process using the cell culture device 10A according to the second embodiment will be described. In the following description, matters overlapping with the freezing process according to the first embodiment will be appropriately omitted. FIG. 12 is a view showing a flow of cells, media, and the like in a case where the cell culture device 10A performs a freezing process, and corresponds to FIG. 6 according to the first embodiment. A correspondence between the flow of cells, media, and the like and each processing step shown below is shown in FIG. 12.

In Step S41, the cells and a used medium are transferred into the storage container 30 from the culture container 20. In Step S42, a concentration process in which the used medium is removed from a mixture containing the cells and the used medium which have been stored in the storage container 30 is performed. The used medium is collected in the waste liquid collection container 16 through the concentration process and the cells stay in the pipe a5.

In Step S43, a freezing liquid accommodated in the freezing liquid accommodating portion 131 flows into the storage container 30 via the flow path F3 and the circulation flow path F1. The freezing liquid is stirred by passing through the stirring portions 51 and 52 within the flow path F3. Thereafter, the on-off valve V14 is made to enter an open state, and the freezing liquid flows out from the storage container 30 and joins to the cells staying in the pipe a5.

In Step S44, the cells and the freezing liquid which have been staying in the pipe a5 are accommodated in the preservation container 17a of the freezing portion 17 via the stirring portion 50 and the flow path F5. The cells and the freezing liquid are stirred and mixed with each other by passing through the stirring portion 50. The freezing portion 17 freezes the cells accommodated in the preservation container 17a together with the freezing liquid.

As described above, in the cell culture device 10A according to the second embodiment, the stirring portion 50 is provided between the outflow port 32 of the storage container 30 and the inflow port 21 of the culture container 20. Accordingly, in the subculture process, the medium exchange process, and the division process, the cells and the medium are stirred and mixed with each other using the stirring portion 50 immediately before being accommodated in the culture container 20. Accordingly, the cells can be accommodated in the culture container 20 in a state where the distance between the cells within a new medium becomes uniform. By making the distance between the cells uniform, it is possible to suppress the fusion of cell aggregations, which causes cell death or cell differentiation, and make the size or the growth rate of the cell aggregations uniform. In addition, by accommodating the cells in the culture container 20 in a state where the distance between the cells within a new medium is uniform, stirring which causes damage to the cells is unnecessary within the culture container 20 or it is possible to prepare a culture environment by performing stirring with minimum power. Accordingly, the cell culture device 10A according to the present embodiment can particularly be used suitably in a case of performing a static culture in which cells are allowed to stand in a floating state within a medium.

[Third Embodiment]

Figure 13:
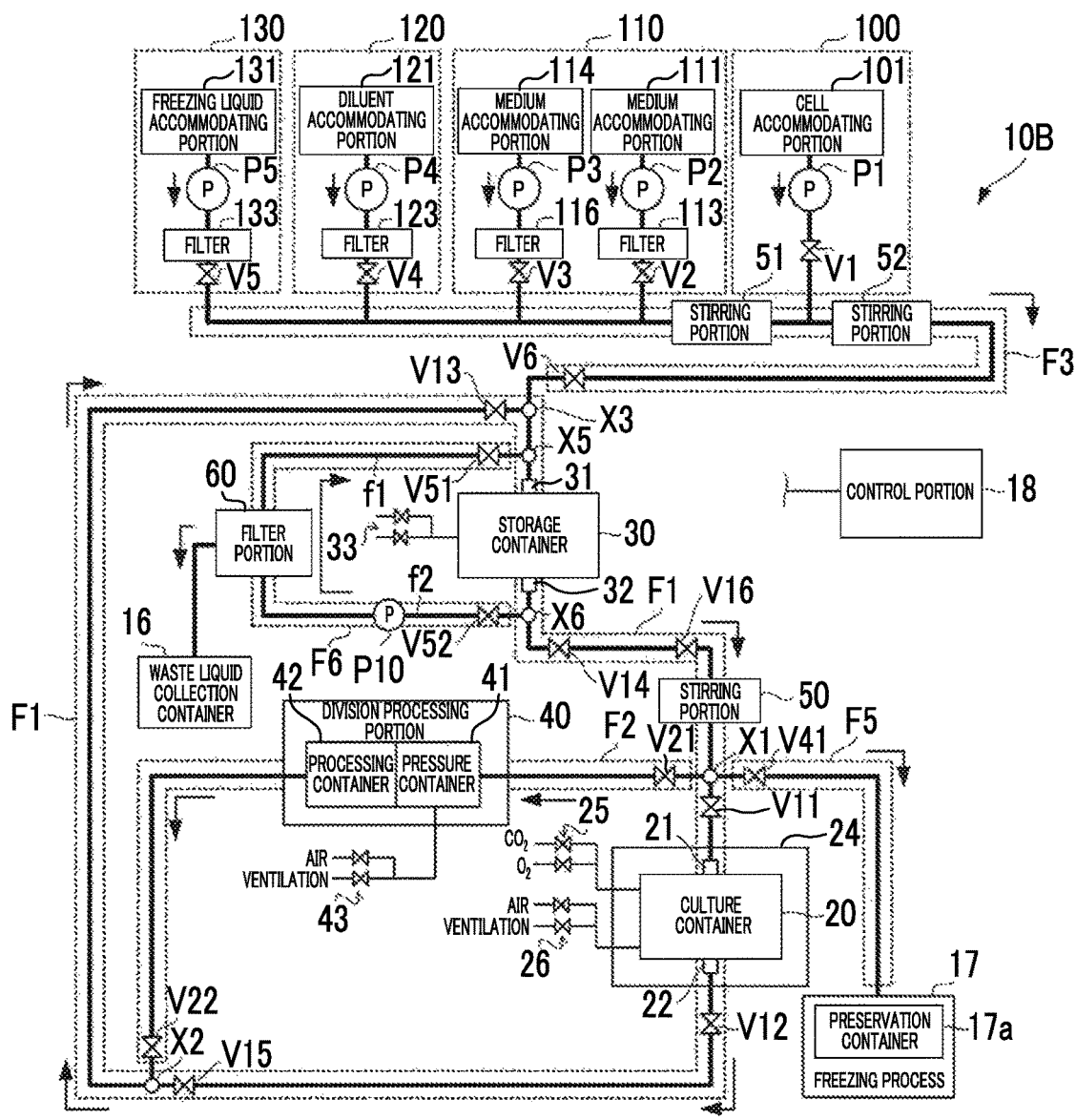
FIG. 13 is a view showing a configuration of a cell culture device according to a third embodiment of the present invention.

FIG. 13 is a view showing a configuration of a cell culture device 10B according to a third embodiment of the present invention. The cell culture device 10B has a configuration in which a flow path F6, a filter portion 60, and a pump P10 are added to the cell culture device 10A according to the above-described second embodiment. The waste liquid collection container 16 is connected to the filter portion 60.

The flow path F6 is a flow path connecting the inflow port 31 to the outflow port 32 of the storage container 30 and includes a pipe f1 connected to the circulation flow path F1 in a connection region X5 and a pipe f2 connected to the circulation flow path F1 in a connection region X6.

The filter portion 60 is provided within the flow path F6 (that is, in the middle of the flow path F6). The filter portion 60 has a function of performing a concentration process of removing a liquid such as a medium, diluent, and a freezing liquid from a mixture containing the cells supplied from the storage container 30 and the above-described liquid.

Figure 14:
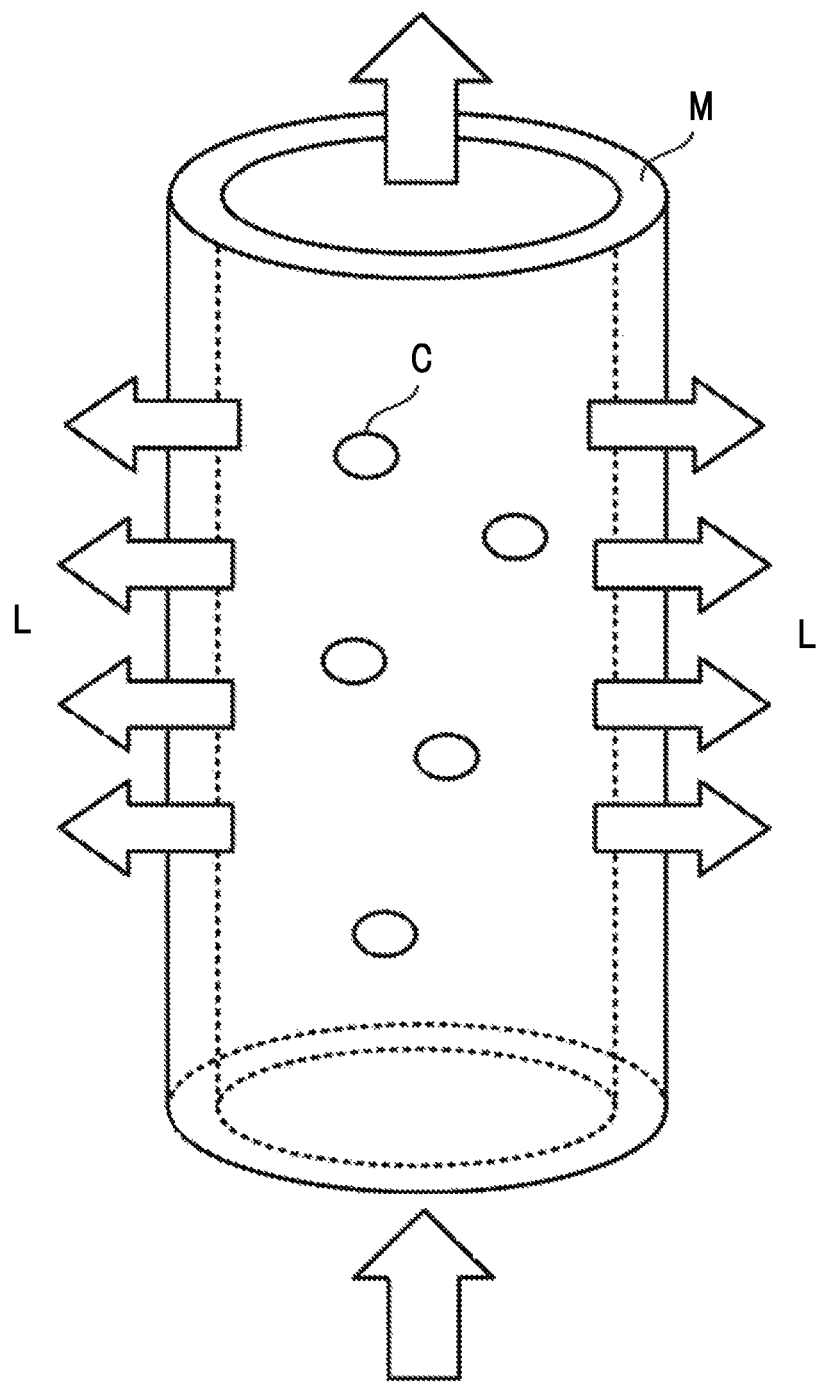
FIG. 14 is a view showing an example of an aspect of filtration in a filter portion according to the embodiment of the present invention.

The filter portion 60 may have a configuration of, for example, a so-called tangential flow filter. The filter portion 60 is configured such that the mixture containing the cells and a liquid such as a medium flows along the surface of a filtration film within the filter portion 60. FIG. 14 is a view showing an example of an aspect of the filtration using the filter portion 60. The filter portion 60 has a filtration film M formed of, for example, hollow fiber. The filtration film M may be a porous film and the material of the filtration film M may be metal, a polymer, or a ceramic sintered body. Gamma ray sterilization or a single use is possible by forming the filtration film M, for example, with a polymer, which is preferable. If a mixture containing cells C and a liquid L, such as a medium, flows into the filtration film M, the liquid L is accommodated in the waste liquid collection container 16 after being discharged to the outside of the filtration film M. In contrast, the cells C are collected in the storage container 30 after passing through the inside of the filtration film M. By performing filtration by tangential flow, it is possible to minimize damage on the cells. The filter portion 60 may have a configuration of a dead-end flow filter in which the flow direction of a mixture containing the cells, a medium, and the like becomes a direction intersecting with the surface of the filtration film.

The pump P10 disposed within the pipe f2 forming the flow path F6 is driven in a case of transferring a mixture containing the cells, a medium, and the like to the filter portion 60 from the storage container 30 and to the storage container 30 from the filter portion 60.

An on-off valve V51 is provided in the vicinity of the connection region X5 within the pipe f1 forming the flow path F6. In addition, an on-off valve V52 is provided in the vicinity of the connection region X6 within the pipe f2 forming the flow path F6. The on-off valves V51 and V52 are made to enter an open state during a period in which cells are collected in the storage container 30 after performing a concentration process in the filter portion 60 and are made to enter a closed state in other cases.

The flow path F6 is an example of a third flow path in the present invention. The filter portion 60 is an example of a first filter portion in the present invention.

Hereinafter, a subculture process, a medium exchange process, a division process, and a freezing process which can be performed in the cell culture device 10B according to the third embodiment will be described. The subculture process, the medium exchange process, the division process, and the freezing process described below are realized by the control portion 18 controlling the operation of the on-off valves V1 to V5, V11 to V16, V21, V22, V31, V41, V51, and V52, the pumps P1 to P5 and P10, and the pressure adjustment mechanisms 26 and 43.

<Subculture Process>

Figure 15:
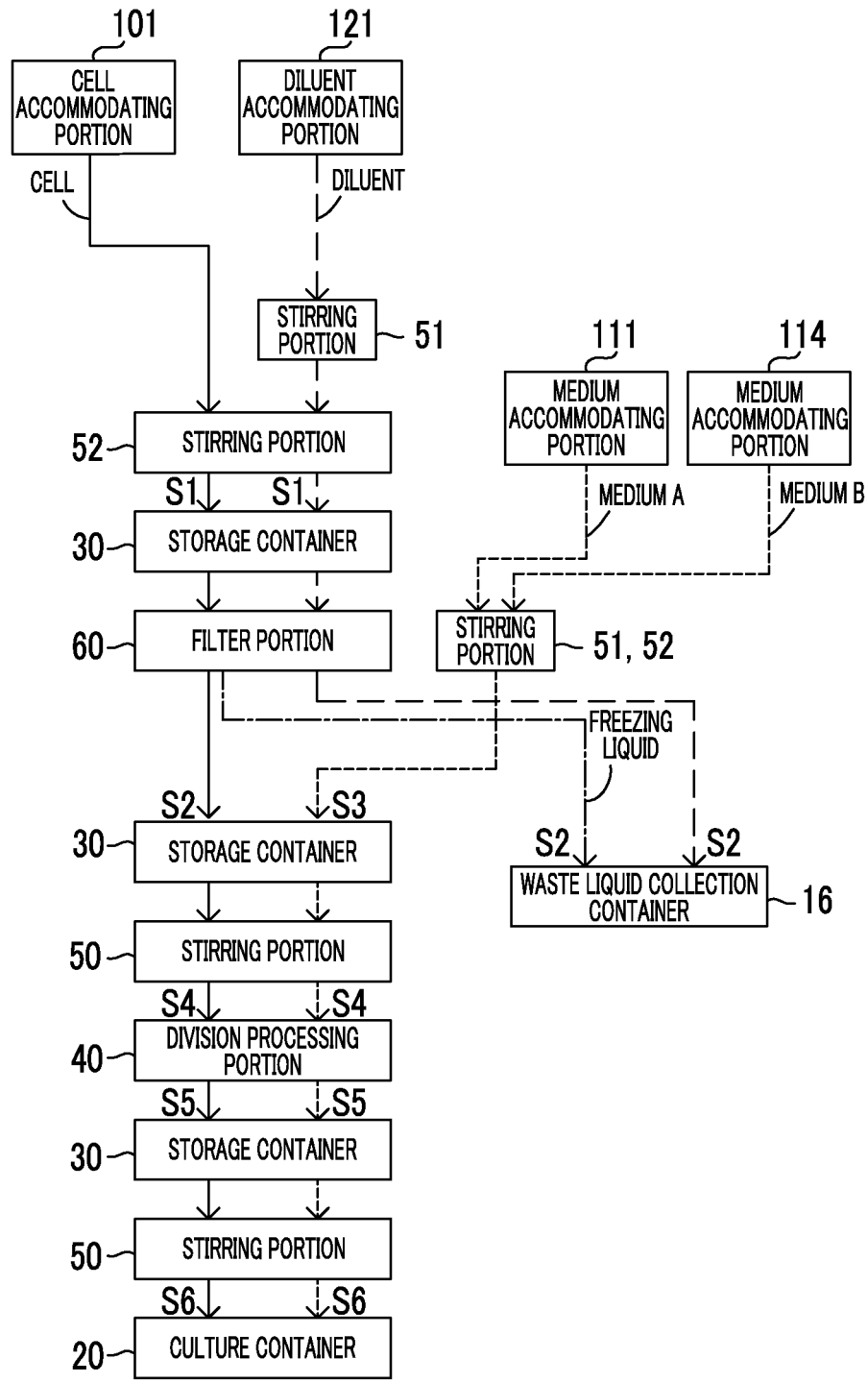
FIG. 15 is a view showing a flow of cells or the like in a case of performing a subculture process in the cell culture device according to the third embodiment of the present invention.

Hereinafter, a subculture process using the cell culture device 10B of the third embodiment will be described. In the following description, a case where a division process in the division processing portion 40 is a mechanical division process will be exemplified. In addition, in the following description, matters overlapping with the subculture process according to the first embodiment will be appropriately omitted. FIG. 15 is a view showing a flow of cells, media, and the like in a case where the cell culture device 10B performs a subculture process, and corresponds to FIG. 2 according to the first embodiment. A correspondence between the flow of cells, media, and the like and each processing step shown below is shown in FIG. 15.

In Step S1, cells accommodated in the cell accommodating portion 101 in a frozen state and diluent accommodated in the diluent accommodating portion 121 flow into the storage container 30 via the flow path F3 and the circulation flow path F1. The cells and the diluent are stirred and mixed with each other by passing through the stirring portion 52 within the flow path F3.

In Step S2, the on-off valves 51 and 52 are made to enter an open state and the pump P10 is driven. Accordingly, the mixture which contains the cells, the freezing liquid, and the diluent and is stored in the storage container 30, the freezing liquid and the diluent accompanying the cells, flows into the filter portion 60. The filter portion 60 performs a concentration process of removing the freezing liquid and the diluent from the mixture containing the cells, the freezing liquid, and the diluent. The freezing liquid and the diluent are collected in the waste liquid collection container 16, and the cells subjected to the concentration process are collected in the storage container 30.

In Step S3, a medium A and a medium B which have been accommodated in the medium accommodating portions 111 and 114 flow into the storage container 30 via the flow path F3 and the circulation flow path F1 and joins to the cells stored in the storage container 30. The medium A and the medium B are stirred and mixed with each other by passing through the stirring portions 51 and 52.

In Step S4, the cells and the medium which have been stored in the storage container 30 are transferred into the division processing portion 40 via the stirring portion 50. The cells flowing into the division processing portion 40 are subjected to a division process within the processing container 42. Accordingly, the cells in a frozen state are divided.

In Step S5, the cells subjected to the division process are transferred into the storage container 30 together with the medium.

In Step S6, the cells and the medium which have been stored in the storage container 30 flow into the culture container 20 via the stirring portion 50. The cells and the medium are stirred and mixed with each other by passing through the stirring portion 50. Accordingly, cells which have been supplied from the cell supply portion 100 are accommodated in the culture container 20 in a state where the distance between the cells in the medium becomes uniform.

In the above-described example, the concentration process in the filter portion 60 is performed once. However, the number of times of performing the concentration process may be set to twice or more as necessary by repeatedly circulating a mixture containing the cells and a used medium between the storage container 30 and the filter portion 60. In addition, in the above-described example, the concentration process and the supply of a new medium in the filter portion are performed before the division process. However, the concentration process and the supply of a new medium in the filter portion may be performed after the division process.

<Medium Exchange Process>

Figure 16:
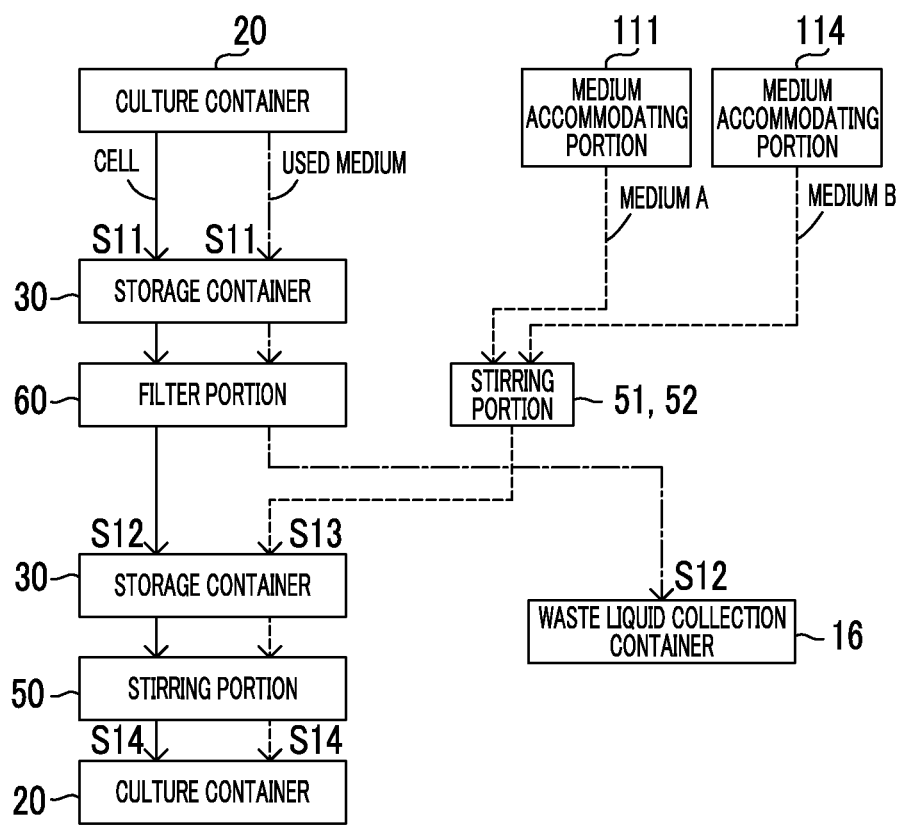
FIG. 16 is a view showing a flow of cells or the like in a case of performing a medium exchange process in the cell culture device according to the third embodiment of the present invention.

Hereinafter, a medium exchange process using the cell culture device 10B according to the third embodiment will be described. In the following description, matters overlapping with the medium exchange process according to the first embodiment will be appropriately omitted. FIG. 16 is a view showing a flow of cells, media, and the like in a case where the cell culture device 10B performs a medium exchange process, and corresponds to FIG. 3 according to the first embodiment. A correspondence between the flow of cells, media, and the like and each processing step shown below is shown in FIG. 16.

In Step S11, the cells and a used medium are transferred into the storage container 30 from the culture container 20. In Step S12, the on-off valves 51 and 52 are made to enter an open state and the pump P10 is driven. Accordingly, the mixture containing the cells and the used medium which have been stored in the storage container 30 flows into the filter portion 60. The filter portion 60 performs a concentration process of removing the used medium from the mixture containing the cells and the used medium. The used medium is collected in the waste liquid collection container 16, and the cells subjected to the concentration process are collected in the storage container 30.

In Step S13, a new medium A and a new medium B which have been accommodated in the medium accommodating portions 111 and 114 flow into the storage container 30 via the flow path F3 and the circulation flow path F1 and join to the cells stored in the storage container 30. The medium A and the medium B are stirred and mixed with each other by passing through the stirring portions 51 and 52.

In Step S14, the cells and the new medium which have been stored in the storage container 30 flow into the culture container 20 via the stirring portion 50. The cells and the new medium are stirred and mixed with each other by passing through the stirring portion 50. Accordingly, cells are accommodated in the culture container 20 in a state where the distance between the cells floating in the medium becomes uniform.

In the above-described example, the concentration process in the filter portion 60 is performed once. However, the number of times of performing the concentration process may be set to twice or more as necessary by repeatedly circulating a mixture containing the cells and a used medium between the storage container 30 and the filter portion 60.

<Division Process>

Figure 17:
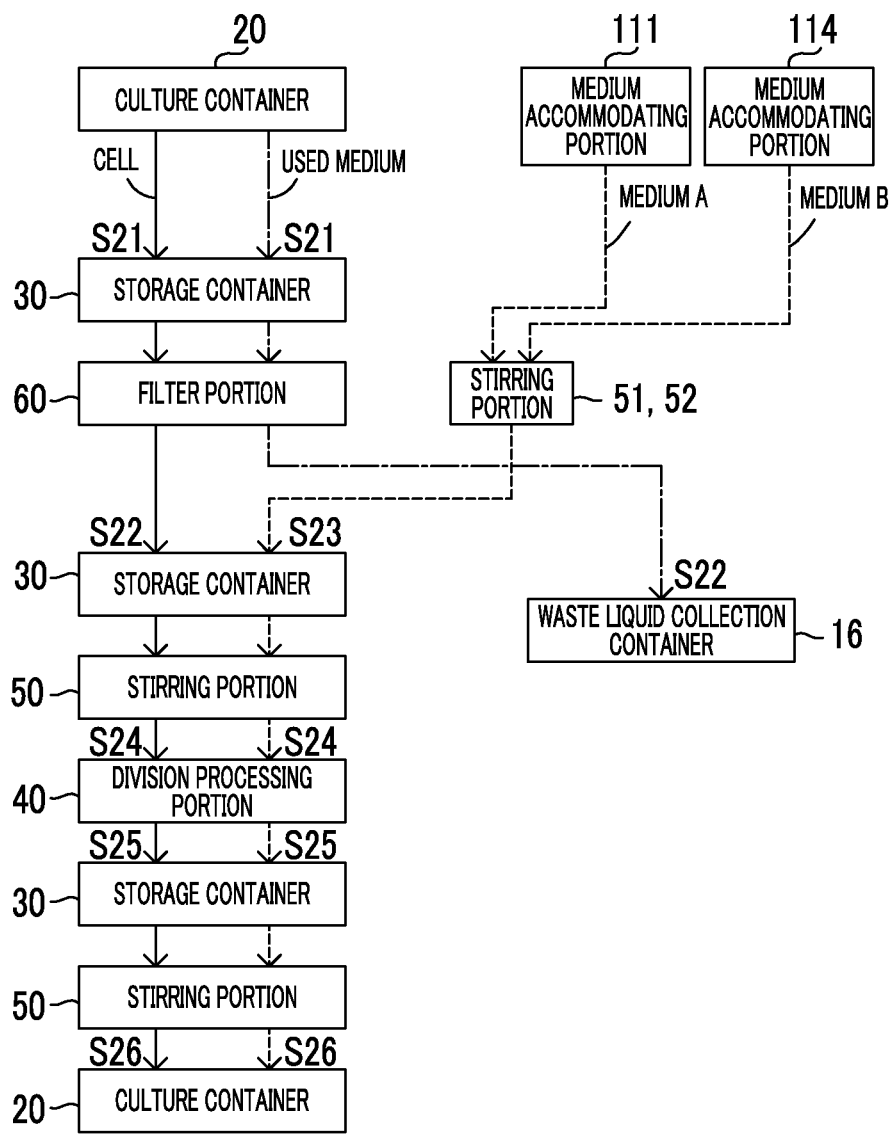
FIG. 17 is a view showing a flow of cells or the like in a case of performing a division process in the cell culture device according to the third embodiment of the present invention.

Hereinafter, a division process using the cell culture device 10B according to the third embodiment will be described. In the following description, a case where a division process in the division processing portion 40 is a mechanical division process will be exemplified. In addition, in the following description, matters overlapping with the division process according to the first embodiment will be appropriately omitted. FIG. 17 is a view showing a flow of cells, media, and the like in a case where the cell culture device 10B performs a division process, and corresponds to FIG. 4 according to the first embodiment. A correspondence between the flow of cells, media, and the like and each processing step shown below is shown in FIG. 17.

In Step S21, cells and a used medium are transferred into the storage container 30 from the culture container 20. In Step S22, on-off valves 51 and 52 are made to enter an open state and the pump P10 is driven. Accordingly, the mixture containing the cells and the used medium which have been stored in the storage container 30 flows into the filter portion 60. The filter portion 60 performs a concentration process of removing the used medium from the mixture containing the cells and the used medium. The used medium is collected in the waste liquid collection container 16, and the cells subjected to the concentration process are collected in the storage container 30.

In Step S23, a new medium A and a new medium B which have been accommodated in the medium accommodating portions 111 and 114 flow into the storage container 30 via the flow path F3 and the circulation flow path F1 and join to the cells stored in the storage container 30. The medium A and the medium B are stirred and mixed with each other by passing through the stirring portions 51 and 52.

In Step S24, the cells and the new medium which have been stored in the storage container 30 are transferred into the division processing portion 40, and a division process is performed on the cell aggregations within the division processing portion 40. In Step S25, the cells subjected to the division process are transferred into the storage container 30 together with the medium.

In Step S26, the cells and the medium which have been stored in the storage container 30 flow into the culture container 20 via the stirring portion 50. The cells and the medium are stirred and mixed with each other by passing through the stirring portion 50. Accordingly, cells are accommodated in the culture container 20 in a state where the distance between the cells floating in the medium becomes uniform.

In the above-described example, the concentration process in the filter portion 60 is performed once. However, the number of times of performing the concentration process may be set to twice or more as necessary by repeatedly circulating a mixture containing the cells and a used medium between the storage container 30 and the filter portion 60. In addition, in the above-described example, the concentration process and the supply of a new medium in the filter portion are performed before the division process. However, the concentration process and the supply of a new medium in the filter portion may be performed after the division process.

<Freezing Process>

Figure 18:
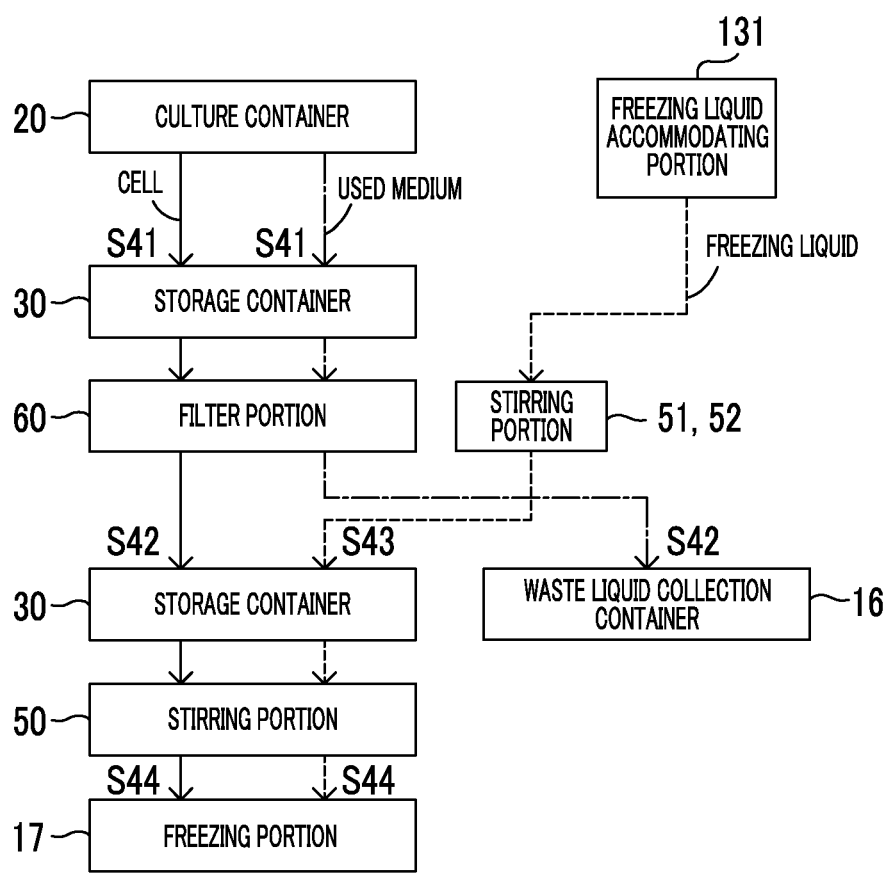
FIG. 18 is a view showing a flow of cells or the like in a case of performing a freezing process in the cell culture device according to the third embodiment of the present invention.

Hereinafter, a freezing process using the cell culture device 10B according to the third embodiment will be described. In the following description, matters overlapping with the freezing process according to the first embodiment will be appropriately omitted. FIG. 18 is a view showing a flow of cells, media, and the like in a case where the cell culture device 10B performs a freezing process, and corresponds to FIG. 6 according to the first embodiment. A correspondence between the flow of cells, media, and the like and each processing step shown below is shown in FIG. 18.

In Step S41, cells and a used medium are transferred into the storage container 30 from the culture container 20. In Step S42, the on-off valves 51 and 52 are made to enter an open state and the pump P10 is driven. Accordingly, the mixture containing the cells and the used medium which have been stored in the storage container 30 flows into the filter portion 60. The filter portion 60 performs a concentration process of removing the used medium from the mixture containing the cells and the used medium. The used medium is collected in the waste liquid collection container 16, and the cells subjected to the concentration process are collected in the storage container 30.

In Step S43, a freezing liquid accommodated in the freezing liquid accommodating portion 131 flows into the storage container 30 via the flow path F3 and the circulation flow path F1 and joins to the cells stored in the storage container 30. The freezing liquid is stirred by passing through the stirring portions 51 and 52.

In Step S44, the cell and the freezing liquid which have been stored in the storage container 30 are accommodated in the preservation container 17a of the freezing portion 17 via the stirring portion 50 and the flow path F5. The cells and the freezing liquid are stirred and mixed with each other by passing through the stirring portion 50. The freezing portion 17 freezes the cells accommodated in the preservation container 17a together with the freezing liquid.

In the above-described example, the concentration process in the filter portion 60 is performed once. However, the number of times of performing the concentration process may be set to twice or more as necessary by repeatedly circulating a mixture containing the cells and a used medium between the storage container 30 and the filter portion 60.

In the cell culture device 10B according to the third embodiment, a concentration process is performed by making a mixture containing cells, media, and the like pass through the filter portion 60 as described above. Accordingly, a precipitation process is unnecessary in which cells are precipitated within the storage container 30. Accordingly, it is possible to improve the efficiency of a concentration process as compared to the cell culture devices 10 and 10A according to the first and second embodiments.

[Fourth Embodiment]

Figure 19:
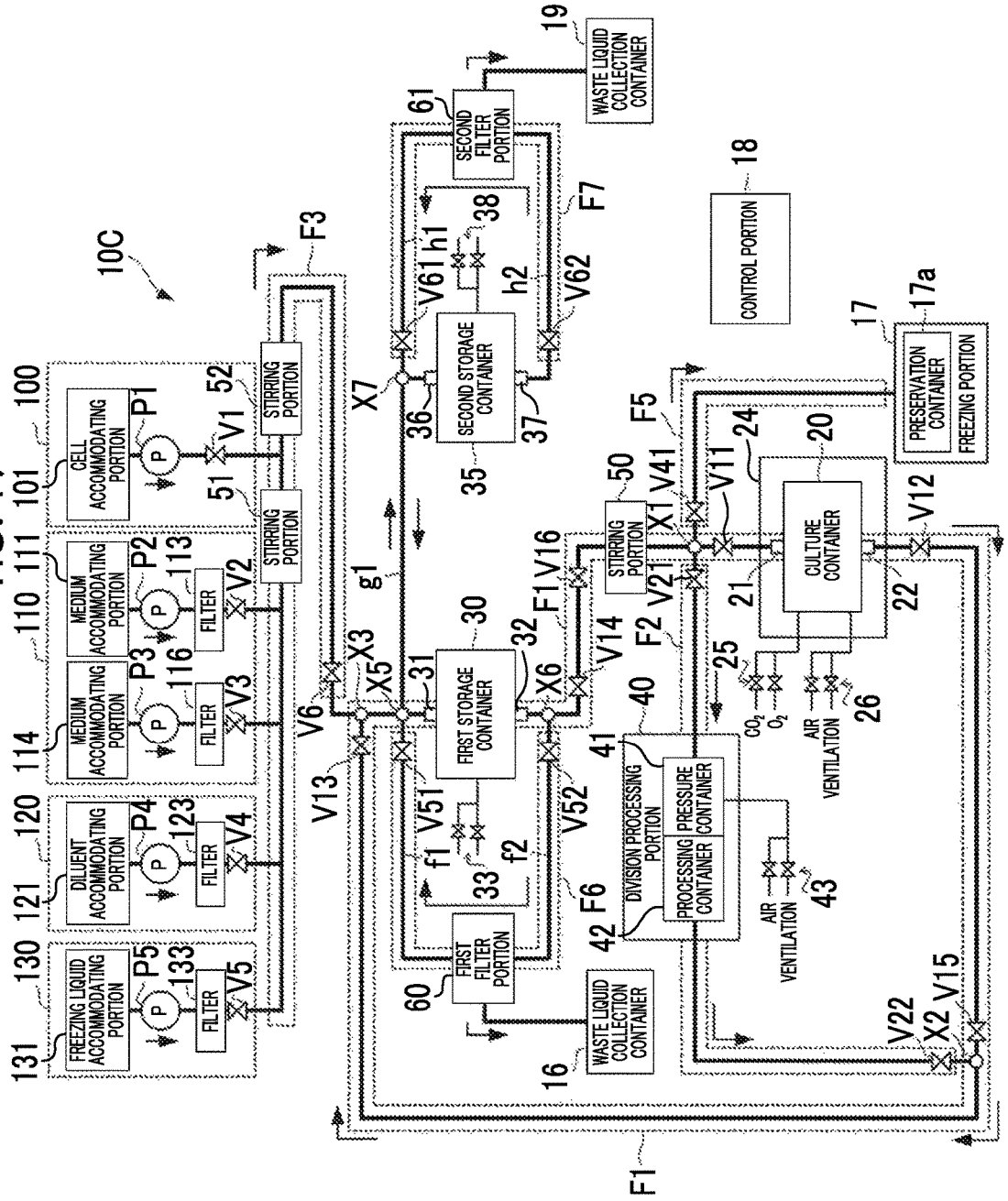
FIG. 19 is a view showing a configuration of a cell culture device according to a fourth embodiment of the present invention.

FIG. 19 is a view showing a configuration of a cell culture device 10C according to a fourth embodiment of the present invention. The cell culture device 10C has a configuration in which a second storage container 35 and a second filter portion 61 are added to the cell culture device 10B according to the third embodiment. In addition, a waste liquid collection container 19 is connected to the second filter portion 61. The first storage container and the first filter portion 60 in the cell culture device 10C correspond to the storage container 30 and the filter portion 60 according to the third embodiment.

The second storage container 35 has the same configuration as that of the first storage container 30 and has an inflow port 36 and an outflow port 37. The inflow port 36 of the second storage container 35 is connected to the inflow port 31 of the first storage container 30 through a pipe g1 connected to the circulation flow path F1 in a connection region X7. A flow path F7 is a flow path connecting the inflow port 36 to the outflow port 37 of the second storage container 35 and includes pipes h1 and h2.

The second filter portion 61 is provided within the flow path F7 (that is, in the middle of the flow path F7). Similarly to the first filter portion 60, the second filter portion 61 has a function of performing a concentration process of removing a liquid, such as a medium accompanying the cells, from a mixture containing the cells supplied from the second storage container 35 and the above-described liquid. Similarly to the first filter portion 60, the second filter portion 61 may have a configuration of a tangential flow filter. A waste liquid such as a medium discharged from the second filter portion 61 is collected in the waste liquid collection container 19.

An on-off valve V61 is provided in the vicinity of the connection region X7 in the pipe h1 forming the flow path F7. In addition, an on-off valve V62 is provided in the vicinity of the outflow port 37 of the second storage container 35 in the pipe h2 forming the flow path F7.

In addition, the pressure adjustment mechanism 33 included in the first storage container 30 is used in the cell culture device 10C according to the present embodiment without using a pump as means for transferring a mixture containing cells, media, and the like from the first storage container 30 and the first filter portion 60. Similarly, a pressure adjustment mechanism 38 included in the second storage container 35 is used without using a pump as means for transferring a mixture containing cells, media, and the like from the second storage container 35 and the second filter portion 61.

The first storage container 30 is an example of a first storage container in the present invention. The second storage container 35 is an example of a second storage container in the present invention. The inflow port 36 of the second storage container 35 is an example of a third inflow port in the present invention. The outflow port 37 of the second storage container 35 is an example of a third outflow port in the present invention. The second filter portion 61 is an example of a second filter portion in the present invention. The flow path F7 is an example of a fourth flow path in the present invention. The pressure adjustment mechanism 33 is an example of a first pressure adjustment mechanism included in the first storage container in the present invention. The pressure adjustment mechanism 38 is an example of a second pressure adjustment mechanism included in the second storage container in the present invention.

In the cell culture device 10C according to the present embodiment, it is possible to continuously perform a concentration process by alternately using a first concentration processing unit including the first storage container 30 and the first filter portion 60 and a second concentration processing unit including the second storage container 35 and the second filter portion 61.

Figure 20:
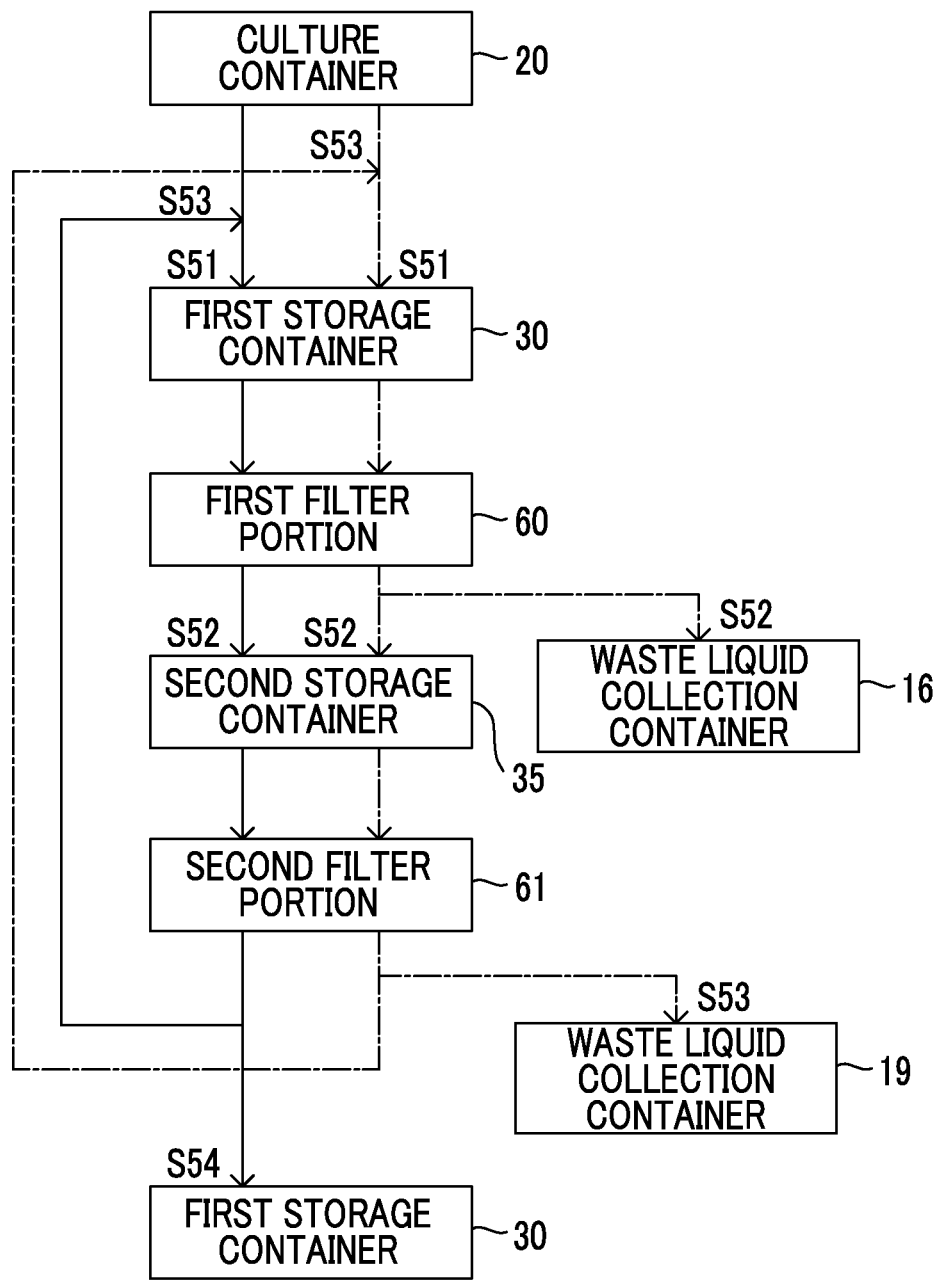
FIG. 20 is a view showing a flow of cells or the like in a case of performing a concentration process in the cell culture device according to the fourth embodiment of the present invention.

Hereinafter, the concentration process using the cell culture device 10C according to the fourth embodiment will be described. In the description below, a concentration process performed during a medium exchange process will be exemplified. FIG. 20 is a view showing a flow of cells, media, and the like in a case where the cell culture device 10C according to the present embodiment performs a concentration process. A correspondence between the flow of cells, media, and the like and each processing step shown below is shown in FIG. 20.

In Step S51, the cells and a used medium are transferred into the first storage container 30 from the culture container 20. In Step S52, the on-off valves 51 and 52 are made to enter an open state. In addition, the atmosphere within the first storage container 30 is pressurized by the pressure adjustment mechanism 33. In contrast, the atmosphere within the second storage container 35 is released into the air by the pressure adjustment mechanism 38. Accordingly, the air pressure within the first storage container 30 increases and a mixture containing the cells and the used medium which have been stored in the first storage container 30 flows into the first filter portion 60. A part of the used medium is removed from the mixture containing the cells and the used medium through the concentration process performed by the first filter portion 60 and is collected in the waste liquid collection container 16. Thereafter, a mixture containing the cells and the remaining used medium flows into the second storage container 35 via the pipe g1.

In Step S53, the on-off valves V61 and V62 are made to enter an open state. In addition, the atmosphere within the second storage container 35 is pressurized by the pressure adjustment mechanism 38. In contrast, the atmosphere within the first storage container 30 is released into the air by the pressure adjustment mechanism 33. Accordingly, the air pressure within the second storage container 35 increases and a mixture containing the cells and the used medium which have been stored in the second storage container 35 flows into the second filter portion 61. A part of the used medium is removed from the mixture containing the cells and the used medium through the concentration process performed by the second filter portion 61 and is collected in the waste liquid collection container 19. Thereafter, a mixture containing the cells and the remaining used medium flows into the first storage container 30 via the pipe g1.

Thereafter, the process of Steps S52 and S53 is repeatedly performed as necessary. Accordingly, a used medium is removed from a mixture containing the cells and the used medium. The cells subjected to the concentration process are stored in the first storage container 30 in Step S54.

In the above-described description, the concentration process performed during a medium exchange process has been exemplified. However, the above-described concentration process can also be applied to a concentration process performed during a subculture process, a division process, and a freezing process.

According to the cell culture device 10C of the fourth embodiment, the concentration process is performed in the first filter portion 60 and the second filter portion 61, and therefore, a precipitation process is unnecessary in which cells are precipitated within a storage container. In addition, according to the cell culture device 10C, the concentration process is performed by alternately using the first concentration processing unit and the second concentration processing unit, and therefore, the transfer of cells, media, and the like between the first concentration processing unit and the second concentration processing unit can be performed through feeding pressure using the pressure adjustment mechanisms 33 and 38. Accordingly, it is possible to perform the concentration process without using a liquid contact pump and reduce the damage to cells as compared to the case of using a liquid contact pump. In the present embodiment, the case of alternately using the first concentration processing unit and the second concentration processing unit has been exemplified. However, the first concentration processing unit and the second concentration processing unit may be used at the same time. That is, in this case, concentration processes are performed side by side within the first concentration processing unit and the second concentration processing unit.

[First Modification Example]

Various modifications are possible in the configurations of the cell culture devices according to the above-described first to fourth embodiments.

Figure 21:
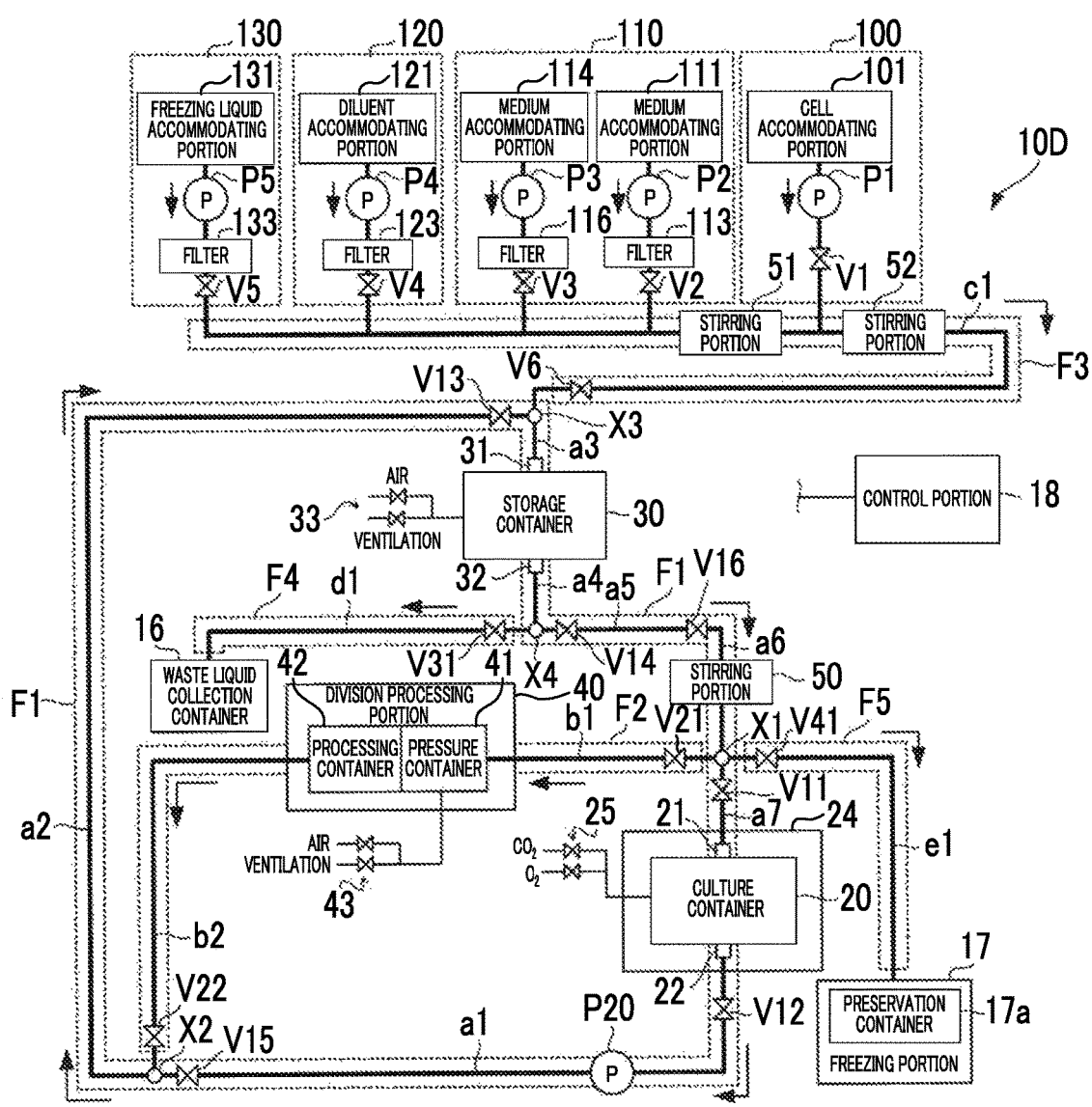
FIG. 21 is a view showing a configuration of a cell culture device according to another embodiment of the present invention.

FIG. 21 is a view showing a configuration of a cell culture device 10D according to a first modification example. The cell culture device 10D has a pump P20 as means for transferring the cells and media to the storage container 30 from the culture container 20.

In a case where the culture container 20, for example, has a form of a plastic bag, it can be difficult to pressurize the atmosphere inside the culture container 20 using the pressure adjustment mechanism 26 due to pressure resistance performance of a container main body. The pump P20 can be applied to the case where it is difficult to pressurize the atmosphere inside the culture container 20 in this manner.

The pump P20 is preferably disposed between the connection region X2 and the outflow port 22 of the culture container 20 within the circulation flow path F1 as shown in FIG. 21. It is considered that cells receive damage from a division process in the division processing portion 40. In addition, if damage is further given to the cells immediately after the division process, there is a concern that cell viability may decrease. That is, there is a concern that damage may be accumulated within the cells passing through a pump after the division process, and therefore, cell viability may decrease. According to the cell culture device 10D of this modification example, the pump P20 is disposed between the connection region X2 and the outflow port 22 of the culture container 20, and therefore, the cells subjected to a division process in the division processing portion 40 are accommodated in the culture container 20 without passing through a pump.

A case where the pump P20 is applied to the cell culture device 10A of the second embodiment has been shown in FIG. 21. However, the pump P20 can also be applied to the cell culture devices 10, 10B, and 10C according to the first, third, and fourth embodiments.

[Second Modification Example]

Figure 22:
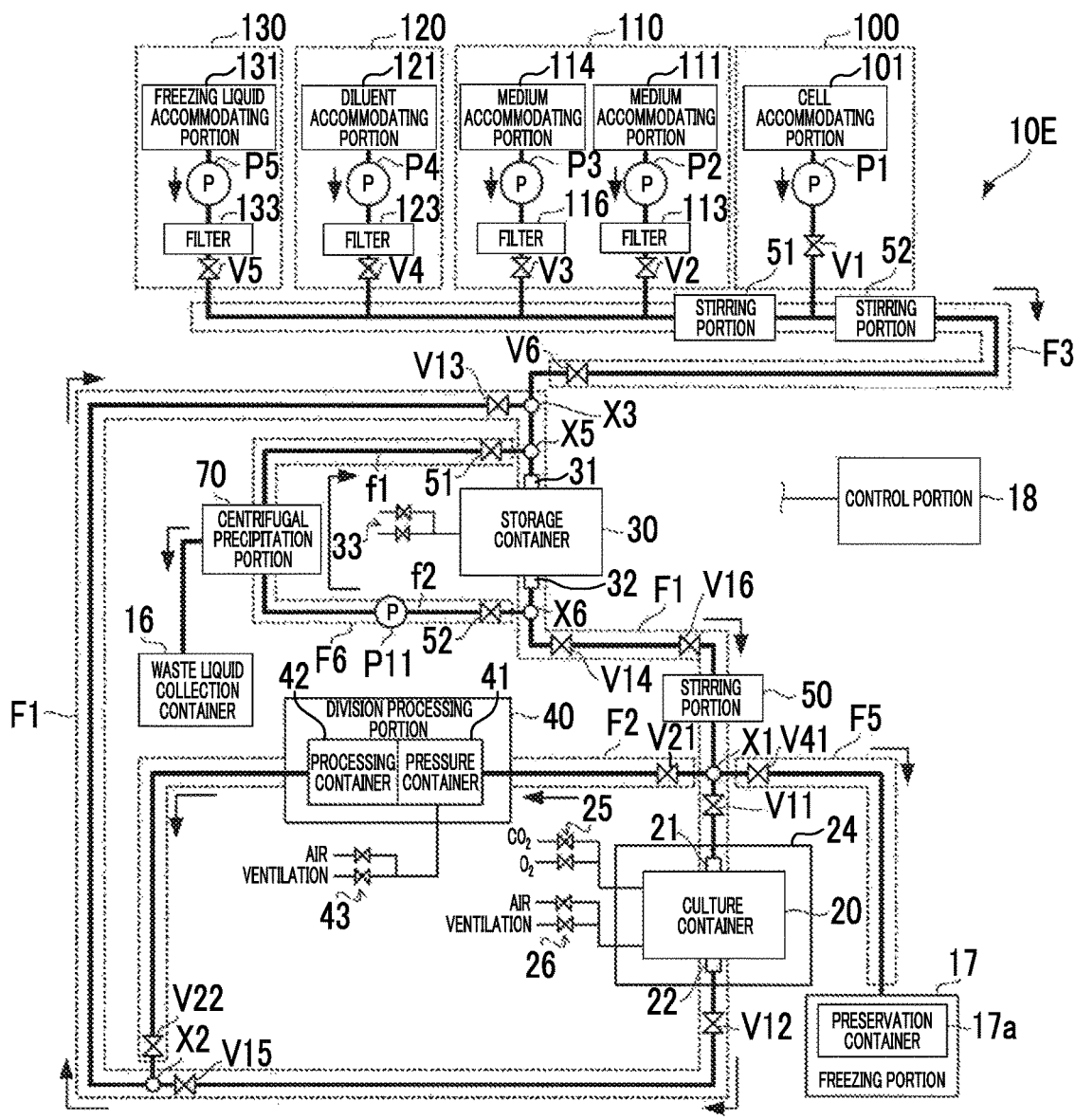
FIG. 22 is a view showing a configuration of a cell culture device according to still another embodiment of the present invention.

FIG. 22 is a view showing a configuration of a cell culture device 10E according to a second modification example. The cell culture device 10E has a configuration in which the filter portion 60 in the cell culture device 10B according to the third embodiment is replaced by a centrifugal precipitation portion 70.

Similarly to the filter portion 60, the centrifugal precipitation portion 70 has a function of performing a concentration process of removing a liquid such as a used medium from a mixture containing the cells and the liquid. The centrifugal precipitation portion 70 centrifugally separates a liquid such as a medium from the cells using the difference in specific gravity between the cells and the liquid such as a medium, and discharges the liquid such as a medium into the waste liquid collection container 16.

A configuration may be employed in which the centrifugal precipitation portion 70 and the filter portion 60 are installed side by side so as to selectively use them. In addition, the first filter portion 60 and the second filter portion 61 in the cell culture device 10C according to the fourth embodiment may be respectively replaced with centrifugal precipitation portion 70.

[Third Modification Example]

Figure 23:
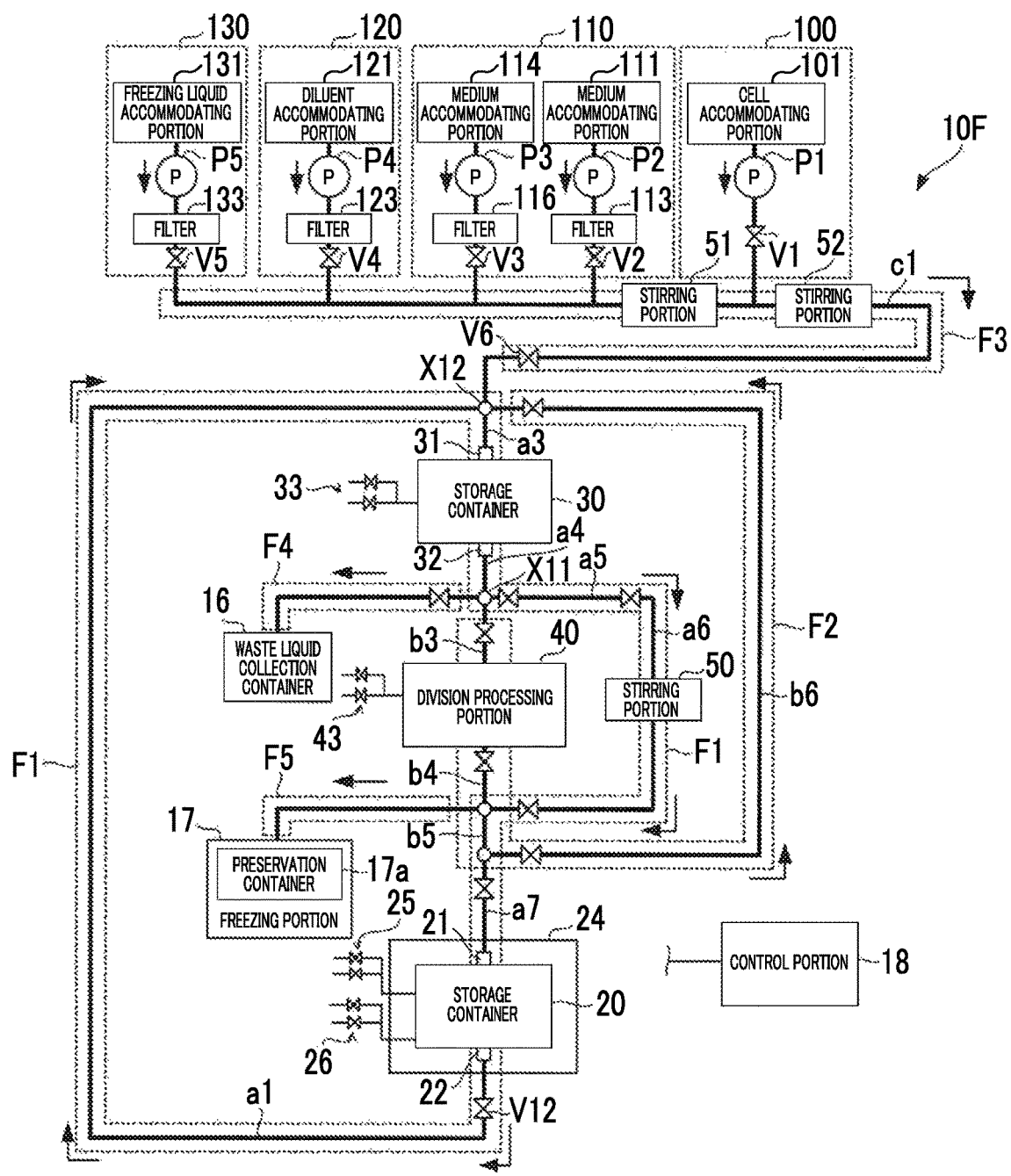
FIG. 23 is a view showing a configuration of a cell culture device according to still another embodiment of the present invention.

FIG. 23 is a view showing a configuration of a cell culture device 10F according to a third modification example. The configuration of each pipe forming the circulation flow path F1 and the flow path F2 in the cell culture device 10F is different from those in the cell culture devices 10 and 10A to 10C according to the above-described first to fourth embodiments.

In the cell culture device 10F, the circulation flow path F1 connecting the inflow port 21 and the outflow port 22 of the culture container 20 includes the pipes a1 to a7 and a pipe b5. The culture container 20, the storage container 30, and the stirring portion 50 are provided in the circulation flow path F1.

The flow path F2 includes pipes b3 to b6 connecting a connection region X11 positioned between the outflow port 32 of the storage container 30 and the inflow port 21 of the culture container 20 within the circulation flow path F1 and a connection region X12 positioned between the inflow port 31 of the storage container 30 and the outflow port 22 of the culture container 20 in the circulation flow path F1. Cells, media, and the like flowing into the circulation flow path F1 can flow into the flow path F2 via the connection region X11. In addition, the cells, the media, and the like flowing into the flow path F2 can flow into the circulation flow path F1 via the connection region X12. The division processing portion 40 is provided within the flow path F2.

The circulation flow path F1 is an example of a first flow path in the present invention. The flow path F2 is an example of a second flow path in the present invention. The connection region X11 is an example of a first region in the present invention. The connection region X12 is an example of a second region in the present invention.

According to the cell culture device 10F, it is possible to perform a subculture process, a medium exchange process, a division process, and a freezing process similarly to those in the cell culture devices 10 and 10A according to the above-described first and second embodiments. The configuration of the pipe in the cell culture device 10F can also be applied to the cell culture devices 10B and 10C according to the third and fourth embodiments.

The disclosure of Japanese Patent Application No. 2015-008718 filed Jan. 20, 2015 is incorporated in the present specification as a whole by reference. In addition, all of the documents, patent applications, and technical standards described in the present specification are incorporated in the present specification for reference to the same extent as a case where incorporation of individual document, patent application, and technical standard for reference is specifically and individually stated.

What is claimed is:

1. A cell culture device comprising:
   a culture container which has a first inflow port and a first outflow port and is used for culturing cells;
   a first flow path which connects the first outflow port to the first inflow port;
   a first storage container which is a storage container, which is provided within the first flow path and used for storing cells cultured in the culture container, the first storage container having a second inflow port which is connected to the first outflow port and a second outflow port which is connected to the first inflow port;

a second flow path connecting a first region within the first flow path which is positioned between the second outflow port and the first inflow port, and a second region within the first flow path which is positioned between the second inflow port and the first outflow port;

a division processing portion which is provided within the second flow path, performs a division process of dividing a cell aggregation, which is an aggregation of cells cultured in the culture container and flows in from the first flow path via the first region, and allows the cells subjected to the division process to flow out into the first flow path via the second region; and a medium supply portion which supplies a medium to the inside of the first flow path.

2. The cell culture device according to claim 1, further comprising:

a first stirring portion which is provided between the second outflow port and the first inflow port within the first flow path and stirs a fluid flowing in.

3. The cell culture device according to claim 2, wherein the first stirring portion includes a static mixer.

4. The cell culture device according to claim 1, further comprising:

a first filter portion which is provided within a third flow path connecting the second inflow port to the second outflow port and performs a concentration process in which a liquid is removed from a mixture containing cells and the liquid accompanying the cells flowing out from the second outflow port.

5. The cell culture device according to claim 4, wherein the first filter portion includes a tangential flow filter.

6. The cell culture device according to claim 4, further comprising:

a second storage container including a third outflow port and a third inflow port which is connected to the second inflow port; and a second filter portion which is provided within a fourth flow path connecting the third inflow port to the third outflow port and performs a concentration process in which a liquid is removed from a mixture containing cells and the liquid accompanying the cells flowing out from the third outflow port.

7. The cell culture device according to claim 6, wherein the second filter portion includes a tangential flow filter.

8. The cell culture device according to claim 6, wherein the concentration process using the first filter portion and the concentration process using the second filter portion are alternately performed.

9. The cell culture device according to claim 6, further comprising:

a first pressure adjustment mechanism, comprising a first air introducing valve and a first ventilation valve, which adjusts a pressure within the first storage container; and a second pressure adjustment mechanism, comprising a second air introducing valve and a second ventilation valve, which adjusts a pressure within the second storage container.

10. The cell culture device according to claim 1, wherein the division processing portion has a processing container for performing the division process and a third pressure adjustment mechanism, comprising a third air introducing valve and a third ventilation valve, which adjusts a pressure within the processing container.

11. The cell culture device according to claim 1, further comprising:

a second stirring portion which is provided within a fifth flow path connecting the medium supply portion and the first flow path and stirs a fluid flowing in.

12. The cell culture device according to claim 11, further comprising:

a cell supply portion which is connected to a downstream side of the second stirring portion in the fifth flow path and supplies cells cultured in the culture container to the first flow path via the fifth flow path; and a third stirring portion which is provided on a downstream side of a region, to which the cell supply portion is connected, in the fifth flow path and stirs a fluid flowing in.

13. The cell culture device according to claim 1, further comprising:

a cell supply portion which supplies cells cultured in the culture container to the first flow path.

14. The cell culture device according to claim 1, further comprising:

a freezing portion which is connected to a third region positioned between the second outflow port and the first outflow port, within the first flow path and freezes cells.

15. The cell culture device according to claim 1, further comprising:

a pressure adjustment mechanism, comprising an air introducing valve and a ventilation valve, which adjusts a pressure within the culture container.

16. A cell culture method in which the cell culture device according to claim 1 is used, the method comprising:

a medium exchange process of exchanging a used medium which has been used for culture of cells within the culture container with a new medium; and a division process of dividing a cell aggregation formed through culturing cells in the culture container, wherein the medium exchange process includes a step of storing the cells cultured in the culture container in the first storage container together with a used medium, a step of removing the used medium from a mixture containing the cells and the used medium which have been stored in the first storage container, a step of supplying a new medium to the cells stored in the first storage container from the medium supply portion, and a step of accommodating the mixture containing the cells and the new medium in the culture container, and wherein the division process includes a step of dividing the cell aggregation formed within the culture container in the division processing portion, a step of exchanging a used medium which has been used for the culture of cells within the culture container with a new medium before or after dividing the cell aggregation in the division processing portion, and a step of accommodating the mixture containing the divided cells and the new medium in the culture container.

* * * * *